US008440880B2

(12) United States Patent
Corbin et al.

(10) Patent No.: US 8,440,880 B2
(45) Date of Patent: May 14, 2013

(54) *XENORHABDUS* SP. GENOME SEQUENCES AND USES THEREOF

(75) Inventors: David R. Corbin, Chesterfield, MO (US); Barry S. Goldman, Acton, MA (US); Gregory J. Hinkle, Plymouth, MA (US); Joseph E. Huesing, Chesterfield, MO (US); Thomas M. Malvar, Troy, MO (US); Karina C. Krasomil-Osterfeld, Ellisville, MO (US); Steven C. Slater, Acton, MA (US); Sergei Spiridonov, Moscow (RU)

(73) Assignee: Monsanto Technology LLC, St. Louis, MO (US)

( * ) Notice: Subject to any disclaimer, the term of this patent is extended or adjusted under 35 U.S.C. 154(b) by 0 days.

(21) Appl. No.: 13/436,027

(22) Filed: Mar. 30, 2012

(65) Prior Publication Data

US 2012/0185974 A1    Jul. 19, 2012

Related U.S. Application Data

(63) Continuation-in-part of application No. 12/385,507, filed on Apr. 9, 2009, now abandoned, which is a continuation of application No. 12/289,606, filed on Oct. 30, 2008, now abandoned, which is a continuation of application No. 09/897,516, filed on Jun. 29, 2001, now abandoned.

(60) Provisional application No. 60/215,161, filed on Jun. 30, 2000.

(51) Int. Cl.
*A01H 5/00* (2006.01)
*A01H 5/10* (2006.01)
*C12N 1/00* (2006.01)
*C12N 15/11* (2006.01)
*C12N 15/31* (2006.01)
*C12N 15/82* (2006.01)

(52) U.S. Cl.
USPC ........... 800/288; 800/298; 800/278; 800/295; 435/91.1; 435/455; 435/468; 435/419

(58) Field of Classification Search ................. None
See application file for complete search history.

(56) References Cited

U.S. PATENT DOCUMENTS 5,674,516 A    10/1997 Raulston et al.

FOREIGN PATENT DOCUMENTS

WO    97/17432 A1    5/1997

OTHER PUBLICATIONS

Guo et al., "Protein Tolerance to Random Amino Acid Change", Proceedings of the National Academy of Sciences, Jun. 2004, pp. 9205-9210, vol. 101, No. 25.
Charles et al,. "A Molecular Aspect of Symbiotic Interactions between the Weevil Sitophilus Oryzae and Its Endosymbiotic Bacteria: Over-Expression of a Chaperonin", Biochemical and Biophysical Research Communications, 1997, pp. 769-774, vol. 239.
Wu et al., "A Modified *Escherichia coli* Chaperonin (groEL) Polypeptide Synthesized in Tobacco and Targeted to Chloroplasts", Plant Molecular Biology, 1993, pp. 1087-1100, vol. 22.
Akhurst et al, "A numerical taxonomic study of the genus *Xenorhabdus* (*Enterobacteriaceae*) and proposed elevation of the subspecies of X. nematophilus to species", Journal of General Microbiology, 1988, pp. 1835-1845, vol. 134.
Borror et al., Selected Pages from Study of Insects, Sixth Edition, Saunders College Publishing, Harcourt Brace College Publishers, 1992, pp. 284, 285, 312, 313, 370, 271, 588-591.
Bowen et al., "Purification and characterization of a high-molecular-weight insecticidal protein complex produced by the entomopathogenic bacterium *Photorhabdus luminescens*", Applied Enviromental Microbiology, 1998, pp. 3029-3035. vol. 64.
Bowen et al., "Insecticidal toxins from the bacteriaum *Photorahabdus luminescens*", Science, 1998, pp. 2129-2132, vol. 280.
Brown et al., "A novel secreted protein toxin from the insect pathogenic bacterium *Xenorhabdus nematophila*", Journal of Biological Chemistry, 2004, pp. 14595-14601, vol. 279.
Brown et al. "Txp40, a ubiquitous insecticidal toxin protein from *Xenorhabdus* and *Photorhabdus* bacteria", Applied Enviromental Microbiology, 2006, pp. 1653-1662, vol. 72.
Definitions of "identify" and "identity." Merriam-Webster online dictionary, <url://www.merriamwebster.com/dictionary/identify> and <url://www.merriam-webster.com/dictionary/identify>. Retrieved from the Internet Jun. 4, 2008.
Ffrench-Constant et al., "Novel insecticidal toxins from nematode-symbiotic bacteria", Cellular and Molecular Life Sciences, 2000, pp. 528-833, vol. 57.
Joshi et al., "An Insecticidal GroEl Protein with Chitin Binding Activity from *Xenorhabdus nematophila*", Journal of Biological Chemistry, 2008, pp. 28287-28296, vol. 283, No. 42.

*Primary Examiner* — Medina A. Ibrahim
*Assistant Examiner* — Lee A Visone
(74) *Attorney, Agent, or Firm* — Thompson Coburn LLP

(57) ABSTRACT

The present invention relates to a nucleic acid sequences from *Xenorhabdus* that encodes a GroEL protein. The invention encompasses nucleic acid molecules present in non-coding regions as well as nucleic acid molecules that encode proteins, fragments of proteins, tRNA's, fragments of tRNA's, rRNA's and fragments of rRNA's. In addition, protein and fragments of proteins so encoded and antibodies capable of binding the proteins are encompassed by the present invention. The invention also relates to methods of using the disclosed nucleic acid molecules, proteins, fragments of proteins, RNA'S, and antibodies, for example, for gene identification and analysis, and preparation of constructs.

11 Claims, No Drawings

XENORHABDUS SP. GENOME SEQUENCES AND USES THEREOF

CROSS REFERENCE TO RELATED APPLICATIONS

This application is a continuation-in-part (CIP) application of U.S. Non-provisional Application Ser. No. 12/385,507, filed Apr. 9, 2009, which is a continuation of U.S. Non-provisional application Ser. No. 12/289,606, filed Oct. 30, 2008, which is a continuation of U.S. Non-provisional application Ser. No. 09/897,516, filed Jun. 29, 2001, which claims priority of U.S. Provisional Application 60/215,161, filed Jun. 30, 2000. Each of the aforementioned US applications is incorporated herein by reference in its entirety.

FIELD OF THE INVENTION

The present invention relates to genomic nucleic acid sequences from *Xenorhabdus* sp., in particular, and to *Photorhabdus* sp., and includes nucleic acid molecules present in both coding and in non-coding regions. Nucleic acid sequences that encode proteins and/or enzymes and homologues and fragments thereof are encompassed by the invention including but not limited to insect inhibitory proteins, proteins capable of conferring antibiotic resistance, microbial inhibitory proteins including bactericidal, bacteriostatic, fungicidal, and fungistatic proteins, proteins capable of conferring resistance to heavy metals or other toxic compositions, proteins and compositions capable of conferring pharmaceutical advantages such as antineoplastic, acaricidal, anti-inflammatory and anti-ulcerogenic properties, polyketide synthases, transposons and mobile genetic elements and their corresponding transposases, excisases and integrases, phage and phage particle proteins, other useful *Xenorhabdus, Photorhabdus, Serratia, Yersinia, Salmonella, E. coli,* and *Erwinia* sp. protein homologues, ribosomal RNA (rRNA), and transfer RNA (tRNA). In addition, proteins and fragments thereof so encoded and antibodies capable of binding the proteins are encompassed by the present invention. The invention also relates to methods of using the disclosed nucleic acid molecules, proteins, fragments of proteins, and antibodies, for example, for gene identification and analysis, preparation of constructs, transformation of cells with nucleotide compositions disclosed herein to produce *Xenorhabdus* proteins or fragments thereof, in particular novel insect inhibitory, bactericidal, fungicidal and nematicidal proteins.

BACKGROUND OF THE INVENTION

*Xenorhabdus* sp. and *Photorhabdus* sp. strains have previously been shown to produce an array of extracellular proteins and small molecules or secondary metabolites having specialized functions. Among the more commercially interesting are proteins and small molecules having antibiotic properties or proteins which exhibit insect inhibitory activity. A small number of insect inhibitory proteins have previously been identified from these bacteria, symbionts of insect-parasitic nematodes. In view of the biotechnology methods which are now available, such proteins and compositions have great potential for use as biologically safe and effective pest control agents. Unlike chemical pesticide compositions, these proteins have no effect upon the environment in general, can be targeted to direct their effect primarily upon target insect species, and have no effect on non-target species. These proteins are comparable in nature to *Bacillus thuringiensis* (BT) proteins, which are the most widely used biological insect pest control agents derived from various strains of *Bacillus thuringiensis*. BT compositions have been in commercial use for more than twenty years as topically applied insect control agents and more recently genes encoding various BT proteins have been expressed in transgenic plants, and in particular in agronomically important crops such as soybean, corn, wheat, rice, and cotton. However, one issue related to the use of BT proteins is resistance management. The concern is that target insect pests feeding on a plant expressing a single BT protein that is generally effective against that pest species will develop resistance to the protein in some calculable period of time. The answer to this problem has been to include in the plant another BT protein also toxic to the same target pest species. The idea is similar in nature to bacterial resistance management, in that the development of resistance to either of the BT proteins will be delayed because pest will not produce progeny that are resistant to either of the BT proteins, in particular if the two proteins that are expressed in the plant have different modes of action or bind different receptors in the insect midgut. Unfortunately, BT proteins are highly related and often it is difficult to distinguish whether two BT proteins toxic to the same insect species have different modes of action. Thus, even though a great variety of BT proteins have been identified, characterized and categorized into distinct classes of proteins, all appear to act in a very similar fashion. Therefore, a different resistance management strategy which takes advantage of insect inhibitory proteins derived from distinct microbial sources other than *Bacillus thuringiensis* would be desirable. Insect inhibitory proteins isolated from *Xenorhabdus* and *Photorhabdus* species of bacteria seem to have all the prerequisites for the delivery of novel genes for transgenic expression of insect pest inhibiting proteins to provide pest resistance to plants, either alone or in combination with *Bacillus thuringiensis* insecticidal crystal proteins.

*Xenorhabdus* sp. is a Gram-negative bacterium, member of the family of Enterobacteriaceae, and symbiotically associated with nematodes of the genus *Steinernema*. The nematode-bacterial complex can be characterized as an obligate and lethal parasitic relationship, specializing in parasitizing and proliferating in soil insect larvae. Infective, non-feeding stages of these nematodes live in soil and carry their nematode-genus-specific symbiotic bacteria in the gut. It is believed that the nematodes actively search for the appropriate insect host, invade the insect larvae through natural openings or lesions in the cuticle and, once inside the hemolymphe, release their symbiotic bacteria. The nematode-bacterial complex secretes a variety of highly efficient extracellular metabolites and proteins exhibiting insectic inhibitory, bactericidal, fungicidal and nematicidal properties to secure the larval mass as a source of nutrition. An array of extracellular enzymes such as lipases, phospholipases, proteases, nucleases as well as several broad spectrum antibiotics, and antifungal and nematicidal compositions are also secreted (Boemare & Akhurst, J. Gen. Microbiol. 134: 751-761 (1988); Li et al., Can. J. Microbiol. 43(8):770-773 (1997); McInerney et al., J. Nat. Prod. 54(3):774-84 (1991); McInerney et al., J. Nat. Prod. 54(3):785-95 (1991); Sundar and Chang, J. Gen. Microbiol. 139 (Pt 12):3139-48 (1993)). It has been discovered that some compounds secreted by *Xenorhabdus* exhibit anti-neoplastic (U.S. Pat. No. 5,827, 872), acaricidal, anti-inflammatory and anti-ulcerogenic properties (U.S. Pat. No. 4,837,222). U.S. Pat. No. 6,048,838 describes insect inhibitory proteins which exhibit a molecular weight of greater than 100 kDa produced by *Xenorhabdus* sp.

which are orally active against a variety of insect species including the orders Lepidoptera, Coleoptera, Diptera, and Acarina.

The nomenclature and taxonomic characterization of *Xenorhabdus* has recently been subject to innovations in the state of the art. The genus *Photorhabdus* was separated from the genus *Xenorhabdus* in 1993 because of significant differences in biochemical and molecular characterization (Boemare et al., Int. J. Syst. Bacteriol. 43: 249-255 (1993)). *Xenorhabdus* exists of at least 4 known species: *X. nematophilus*, *X. beddingii*, *X. poinarii* and *X. bovienii*. (Brunel et al., Appl. & Environm. Microbiol. 63: 574-580 (1997)). Species of *Xenorhabdus* as well as *Photorhabdus* species can be distinguished from each other by restriction analysis of thermally amplified 16S rRNA genes (Brunel et al., Appl. Environm. Microbiol. 63: 574-580 (1997)).

The genetic diversity of symbiotic *Xenorhabdus* and *Photorhabdus* bacteria associated with entomopathogenic nematodes appears to be quite large. The genus *Xenorhabdus* appears more diverse than the genus *Photorhabdus*, and for both genera, the bacterial genotype diversity is in congruence with the host-nematode taxonomy. It has been found that the occurrence of symbiotic bacterial genotypes was related to the ecological distribution of host nematodes (Fisher-Le Saux et al., Appl. Environ. Microbiol. 64(11):4246-54 (1998)). *Xenorhabdus* bacteria isolated from the same geographical location seem to be more similar to each other, regardless of nematode species than bacteria from one nematode species found in very diverse geographical locations (Liu et al., Intl. J. Syst. Bacteriol. 47:948-951; 1997).

Therefore, there is a great deal of interest in identifying the genes that encode new insect inhibiting proteins, and proteins involved in the biosynthetic pathways of novel antibiotics produced by *Xenorhabdus* and *Photorhabdus* bacteria, as well as other useful proteins. Sequencing of the entire genome of *Xenorhabdus* would facilitate such an endeavor, because it would allow dissection and analysis of the genome into discrete genes encoding proteins having beneficial properties as described herein.

SUMMARY OF THE INVENTION

The present invention provides an isolated and purified nucleic acid molecule having a nucleotide sequence, wherein: (1) the nucleotide sequence hybridizes under stringent conditions to a second isolated and purified nucleic acid molecule comprising SEQ ID NO:1 or the complement thereof; (2) the nucleotide sequence is a portion of SEQ ID NO:1; or (3) the nucleotide sequence is the complement of (1) or (2).

The present invention also provides an isolated and purified nucleic acid molecule comprising a nucleotide sequence, wherein: (1) the nucleotide sequence hybridizes under stringent conditions to a second isolated and purified nucleic acid molecule, wherein the hybridizing portion of the nucleotide sequence of the second nucleic acid molecule encodes a polypeptide or protein having an amino acid sequence of SEQ ID NO:2; (2) the nucleotide sequence encodes a polypeptide or protein, wherein the amino acid sequence of the polypeptide or protein is substantially identical to SEQ ID NO:2; or (3) the nucleotide sequence is the complement of (1) or (2). In alternative embodiments, the amino acid sequence of the above described polypeptide or protein is at least 70% identical, at least 80% identical, at least 85% identical, at least 90% identical, or at least 95% identical to an amino acid sequence of SEQ ID NO:2. In a preferred embodiment, the amino acid sequence of the above described polypeptide or protein is SEQ ID NO:2 or SEQ ID NO:2 with conservative amino acid substitutions.

The present invention further provides a method for obtaining a nucleic acid molecule comprising a nucleotide sequence encoding a polypeptide or protein having an amino acid sequence that is at least 70% identical to SEQ ID NO:2.

The present invention, in another aspect, provides a substantially purified polypeptide or protein comprising an amino acid sequence, wherein the amino acid sequence is defined as follows: (1) the amino acid sequence is encoded by a first nucleotide sequence which specifically hybridizes to the complement of a second nucleotide sequence of SEQ ID NO:1; (2) the amino acid sequence is encoded by a third nucleotide sequence that is at least 50% identical to SEQ ID NO:1; or (3) the amino acid sequence is at least 70% identical to SEQ ID NO:2. In alternative embodiments, the above described third nucleotide sequence is at least 55% identical, at least 60% identical, at least 65% identical, at least 70% identical, at least 75% identical, at least 80% identical, at least 85% identical, at least 90% identical, or at least 95% identical to SEQ ID NO:1; and, the above described third nucleotide sequence is SEQ ID NO:1. In a preferred embodiment, the above described amino acid sequence is at least 70% identical, at least 80% identical, at least 90% identical, or at least 95% identical to SEQ ID NO:2.

The present invention also provides a recombinant construct comprising: (A) a promoter region which functions in a host cell to cause the production of a mRNA molecule; which is operably linked to (B) a structural nucleotide sequence, wherein the structural nucleotide sequence is substantially identical to SEQ ID NO:1; which is operably linked to (C) a 3' non-translated sequence that functions in said cell to cause termination of transcription.

The present invention also provides a recombinant construct comprising: (A) a promoter region which functions in a host cell to cause the production of a mRNA molecule; which is operably linked to (B) a structural nucleotide sequence, wherein the structural nucleotide sequence encodes a polypeptide or protein having an amino acid sequence substantially identical to SEQ ID NO:2; which is operably linked to (C) a 3' non-translated sequence that functions in said cell to cause termination of transcription.

The present invention also provides a recombinant construct comprising: (A) a promoter region which functions in a host cell to cause the production of a mRNA molecule, wherein the promoter region is located within SEQ ID NO:1 or complements thereof; which is linked to (B) a structural nucleotide sequence encoding a polypeptide; which is linked to (C) a 3' non-translated sequence that functions in said cell to cause termination of transcription.

The present invention also provides a transformed cell having an exogenous nucleic acid molecule which comprises: (A) a promoter region which functions in said cell to cause the production of a mRNA molecule; which is operably linked to (B) a structural nucleic acid molecule, wherein the structural nucleotide is substantially identical to SEQ ID NO:1; which is operably linked to (C) a 3' sequence that functions in said cell to cause termination of transcription.

The present invention also provides a transformed cell having an exogenous nucleic acid molecule which comprises: (A) a promoter region which functions in said cell to cause the production of a mRNA molecule; which is operably linked to (B) a structural nucleic acid molecule, wherein the structural nucleotide encodes a polypeptide or protein having an amino acid sequence substantially identical to SEQ ID NO:2; which is operably linked to (C) a 3' sequence that functions in said cell to cause termination of transcription.

The present invention also provides a transformed cell having an exogenous nucleic acid molecule which comprises: (A) a promoter region which functions in said cell to cause the production of a mRNA molecule, wherein the promoter region is located within SEQ ID NO:1 or complements thereof; which is operably linked to (B) a structural nucleotide sequence encoding a polypeptide; which is operably linked to (C) a 3' sequence that functions in said cell to cause termination of transcription.

The present invention also provides a plant cell, a mammalian cell, a bacterial cell, an algal cell, an insect cell and a fungal cell transformed with an isolated nucleic acid molecule of the present invention.

The invention also provides isolated nucleic acid molecules comprising nucleotide sequences encoding polypeptides or proteins exhibiting insect inhibitory activity, wherein said activity is manifested by inhibiting the growth or development of, or contributing substantially to, or causing the death of a Coleopteran, a Dipteran, a Lepidopteran, a Hemipteran, a Hymenopteran, or a sucking and piercing insect or insect larvae thereof. Also provided are nucleotide sequences encoding novel proteins comprising polypeptides which augment the activity of polypeptides exhibiting insect inhibitory activity when fed to Coleopteran, Dipteran, Lepidopteran, Hemipteran, Hymenopteran, or sucking and piercing insects or insect larvae thereof.

The present invention also provides a method for using insect inhibitory proteins for controlling target insect pests, i.e. also known as insect pest control.

The present invention also provides a computer readable medium having recorded thereon one or more of the nucleotide sequences disclosed in the US Patent Application Publication No. 20110167520 A1, which is incorporated herein by reference in its entirety, or the complements thereof.

The present invention also provides a computer readable medium having recorded thereon one or more of the nucleotide sequences encoding a protein or fragment thereof, wherein the amino acid sequence of the protein or fragment thereof is one of those amino acid sequences disclosed in the aforementioned US Patent Application Publication No. 20110167520 A1.

The present invention also provides a method for using the computer media of the present invention in isolating/identifying nucleic acids encoding insect inhibitory proteins, or proteins involved in biosynthesis of antibiotics.

A specific *Xenorhabdus* species, Xs85816, deposited according to the Budapets Treaty on the International Recognition of the Deposit of Microorganisms for the Purpose of Patent Procedures with the Agriculture Research Culture Collection (NRRL) International Depositary Authority at 1815 North University Street, in Peoria, Ill. ZIP 61604 U.S.A. on Jun. 22, 2000 and designated as NRRLB-30306, exhibiting insecticidal activity against piercing and sucking insects and against boll weevil is contemplated as a source for DNA sequences encoding insecticidal proteins, and when formulated into a composition of matter as a spray, powder or emulsion, for the treatment of plants or animals to inhibit insect infestation.

Another aspect of the present invention provides a method for isolating novel *Xenorhabdus* and *Photorhabdus* insect inhibitory species and their symbiont specific host entomopathogenic nematodes, wherein an entomopathogenic nematode containing sample of leaf litter, soil, or other earth derived organic sample is collected, and infested with one or more insect larvae. Insect larvae used for such isolation should be preferred target insect larvae commonly associated with insect infestation or pest pressure. The insect infested sample should be incubated for a period of time in order to allow for nematode ingress into the body(ies) of the target insect larvae, and in order for the symbiont *Xenorhabdus* or *Photorhabdus* insect inhibitory bacteria to be released into the contents of the larvae, and for a period of time such that the bacteria proliferate within the body of the larvae. Preferably, the insect larvae are growth inhibited by the infestation, and more preferably, the infested larvae are killed by the infestation of the entomopathogenic compositions produced from either the nematode or from the symbiont bacteria, or both. The bacteria are subsequently isolated and purified using established culture methods, and the nematode hosts can be similarly isolated and purified, and both isolates can be maintained using various means known in the art. Preferably, the entomopathogenic nematodes selectively target specific insect larvae, and more preferably specific strains of insect larvae, such that any given entomopathogenic nematode species is attracted preferentially to that category and class of insect, and preferably the symbiont insect inhibitory bacterium released into the selectively targeted specific insect larvae body is capable of overwhelming the insect larvae so as to elicit growth inhibition, feeding inhibition, death, or a combination of these effects. Evidence of these effects can be verified by selectively providing isolated and purified bacteria obtained from such entomopathogenic nematode infections, bacterial cell extracts, or culture extracts or compositions, to insect larvae in various types of bioassays, followed by monitoring of the insect larvae in comparison to control larvae in order to establish effective insect inhibition.

Yet another aspect of the present invention is the provision of a kit for isolating novel entomopathogenic nematodes and their symbiont insect inhibitory bacteria.

Additionally, a novel method for assaying *Xenorhabdus* or *Photorhabdus* species for their insect inhibitory effects upon piercing and sucking insects, including *Lygus* species, is provided comprising providing an entomopathogenic nematode composition to such an insect comprising a *Xenorhabdus* species or a *Photorhabdus* species wherein said composition is ingested by said insect through a saculus bounded on one side nearest and accessible to the insect by an insect probosis penetrable membrane and on the opposite side of said insect probosis penetrable membrane by a fluid reservoir, said reservoir forming a single layer, said layer having a first and a second surface, said first surface contacting said insect probosis penetrable membrane on the fluid side of the membrane, and said second surface contacting the first surface of a semipermeable membrane having two surfaces, wherein said semipermeable membrane restricts the molecules which are greater than about 100 K Da, greater than about 115 K Da, greater than about 120 k Da, and/or greater than about 130 k Da, from entry into said fluid reservoir, and wherein said second surface of said semipermeable membrane is contacted by a second fluid reservoir containing said molecules; the inhibition of growth or viability of the insect being monitored upon the ingestion of said molecules by the insect through its probosis.

Another aspect of the present invention is provided by a method for identifying an insect inhibitory protein produced from a *Xenorhabdus* or a *Photorhabdus* species which is specific for inhibiting a particular genus or species of insect larvae. The method consists of exposing a first larvae to a particular genus or species of nematode containing either a *Xenorhabdus* or a *Photorhabdus* species of bacterium so that the nematode is allowed to invade the larvae, and release the bacteria from its gut into the insect larvae haemolymphe. The bacteria are allowed to proliferate for a period of time, generally two or so days, and are subsequently harvested from the larvae heamolymphe and isolated by pure cultured onto indicator agar or other medium selective for identification of the bacterial strain. The bacterial strain are then stored for further use using a variety of means available in the art. The pure cultured bacterial strain is then grown in a specified medium, and the medium is harvested and filtered through a submicron filter to eliminate the presence of the bacterial cells. The protein profile of the filtered medium is then analyzed by a number of means known in the art and compared to the protein profile of medium harvested from the same pure culture of bacteria which were passaged through the haemolymphe of another genus or species of insect larvae. Different proteins appearing in the profile of the medium from the bacteria passaged through the haemolymphe of another genus or species of insect larvae are then isolated and purified. The isolated and purified protein(s) can then be used to produce antibodies directed to the protein(s), said antibodies being useful for identifying genomic DNA clones which express all or a portion of the target protein to which antibodies were raised. Alternatively, N or C-terminal sequence data can be obtained which would allow for the production of redundant oligonucleotides for use as probes to identify genomic DNA sequences obtained from the bacterium which hybridize to the oligonucleotides, presumably also being genomic DNA sequences encoding the protein(s) identified as being different in the profile analysis from the original bacterial strains' profiled proteins. Such proteins, and the genes encoding these proteins, are candidate for being the proteins and genes encoding these proteins which are insect inhibitory and insect species specific.

It is also conceived herein that the nematode may produce proteins or other accessory factors which, when combined with the particular symbiont bacteria, trigger, activate, or enhance the expression of the proper insect specific insect inhibitory protein(s).

A further embodiment of the invention provides a method for selecting one or more insect inhibitory protein exhibiting enhanced insect inhibitory properties directed to the control of a selected insect pest species from a *Xenorhabdus* or a *Photorhabdus* bacterium species. The method consists of infesting an insect pest larvae with an insect pathogenic nematode. The nematode infestation results in the production of juvenile nematodes obtained from the infested insect pest, and a *Xenorhabdus* or a *Photorhabdus* bacterium species isolated and purified from the haemolymphe of the infested insect pest larvae. The isolated and purified bacterium species is grown in liquid broth culture, and the culture broth is isolated and purified away from the bacterium species. The broth is tested for the presence of an insect inhibitory composition. The composition is identified, purified and characterized as one or more proteins. Each protein is used to produce antibodies or N-terminal sequence information. The antibodies are used to screen a recombinant genomic library produced from the genome of the isolated and purified bacterium species, resulting in the identification of one or more clones expressing the protein. The one or more clones expressing the protein can be partially sequenced to obtain DNA sequence information that can be used to scan the genomic library disclosed herein, allowing one or more loci corresponding to the partial sequence within the genome of the bacterium to be identified, as well as the complete coding sequence of the gene encoding the protein exhibiting enhanced insect inhibitory properties directed to the control of a selected insect pest species. The N-terminal sequence is used to screen for the presence of genomic nucleotide sequences encoding the N-terminal sequence from the genomic library described herein, which is used to obtain the full length sequence of the gene encoding the protein exhibiting enhanced insect inhibitory properties directed to the control of a selected insect pest species.

Alternatively, the nematode/bacterial symbiont pair can be infested into two or more different insect pests, the bacterial symbiont from the haemolymphe of each insect pest harvested, isolated and purified, and then each isolate grown in liquid broth culture to produce an extracellular protein profile determinable by size exclusion chromotography, SDS-PAGE, two dimensional gel electrophoresis, or a suitable method known in the art to identify protein or proteins produced by one isolate harvested from one insect pest which are not produced by another isolate harvested from a different pest. The gene or genes encoding the protein or proteins can be identified as described above.

DETAILED DESCRIPTION OF THE INVENTION

In accordance with the present invention it has been discovered that the following compositions comprising *Xenorhabdus* species and *Photorhabdus* species of bacteria commonly symbiotically associated with insect pathogenic nematodes, the individual nematodes, and the nucleic acids and amino acids encoded by the said nucleic acids derived from these bacteria and their host nematodes are surprisingly useful in providing compositions comprising insect inhibitory proteins, proteins capable of conferring antibiotic resistance, microbial inhibitory proteins including bactericidal, bacteriostatic, fungicidal, and fungistatic proteins, proteins capable of conferring resistance to heavy metals or other toxic compositions, proteins and compositions capable of conferring pharmaceutical advantages such as antineoplastic, acaricidal, anti-inflammatory and anti-ulcerogenic properties, polyketide synthases, transposons and mobile genetic elements and their corresponding transposases, excisases, integrases, and invertases, phage and phage particle proteins, other useful proteins homologous to proteins derived from *Xenorhabdus, Photorhabdus, Serratia, Yersinia, Salmonella, E. coli*, and *Erwinia* sp. among others, ribosomal RNA (rRNA), and transfer RNA (tRNA). In addition, antibodies directed to the above mentioned proteins and fragments thereof have been discovered to be of particular utility in the present invention. The invention also relates to methods of using the disclosed nucleic acid molecules, proteins, fragments of proteins, and antibodies, for example, for gene identification and analysis, preparation of constructs, transformation of cells with nucleotide compositions disclosed herein to produce *Xenorhabdus* or *Photorhabdus* proteins or fragments thereof, in particular novel insect inhibitory, bactericidal, fungicidal and nematicidal proteins.

Agents of the Present Invention

Nucleic Acid Molecules

One aspect of the present invention relates to an isolated nucleic acid molecule having a nucleotide sequence, wherein: (1) the nucleotide sequence hybridized under stringent conditions to a second isolated nucleic acid molecule comprising SEQ ID NO:1 or the complements thereof; (2) the nucleotide sequence is a portion of SEQ ID NO:1; or (3) the nucleotide sequence is the complement of (1) or (2).

The term "nucleic acid" means a single or double-stranded polymer of deoxyribonucleotide or ribonucleotide bases read from the 5' to the 3' end. Nucleic acids may also optionally contain synthetic, non-natural or altered nucleotide bases that permit correct read through by a polymerase and do not alter expression of a polypeptide encoded by that nucleic acid.

The term "an isolated nucleic acid" refers to a nucleic acid that is no longer accompanied by some of materials with which it is associated in its natural state or to a nucleic acid the structure of which is not identical to that of any of naturally occurring nucleic acid. Examples of an isolated nucleic acid include: (1) DNAs which have the sequence of part of a naturally occurring genomic DNA molecules but are not flanked by two coding sequences that flank that part of the molecule in the genome of the organism in which it naturally occurs; (2) a nucleic acid incorporated into a vector or into the genomic DNA of a prokaryote or eukaryote in a manner such that the resulting molecule is not identical to any naturally occurring vector or genomic DNA; (3) a separate molecule such as a cDNA, a genomic fragment, a fragment produced by polymerase chain reaction (PCR), or a restriction fragment; (4) recombinant DNAs; and (5) synthetic DNAs. An isolated nucleic acid may also be comprised of one or more segments of cDNA, genomic DNA or synthetic DNA.

The term "nucleotide sequence" refers to both the sense and antisense strands of a nucleic acid as either individual single strands or in the duplex. It includes, but is not limited to, self-replicating plasmids, chromosomal sequences, and infectious polymers of DNA or RNA.

A nucleotide sequence is said to be the "complement" of another nucleotide sequence if they exhibit complete complementarity. As used herein, molecules are said to exhibit "complete complementarity" when every nucleotide of one of the sequences is complementary to a nucleotide of the other.

A "coding sequence" is a nucleotide sequence which is translated into a polypeptide, usually via mRNA, when placed under the control of appropriate regulatory sequences. The boundaries of the coding sequence are determined by a translation start codon at the 5'-terminus and a translation stop codon at the 3'-terminus. A coding sequence can include, but is not limited to, genomic DNA, cDNA, and recombinant polynucleotide sequences.

The term "recombinant DNAs" refers to DNAs that contains a genetically engineered modification through manipulation via mutagenesis, restriction enzymes, and the like.

The term "synthetic DNAs" refers to DNAs assembled from oligonucleotide building blocks that are chemically synthesized using procedures known to those skilled in the art. These building blocks are ligated and annealed to form DNA segments which are then enzymatically assembled to construct the entire DNA. "Chemically synthesized", as related to a sequence of DNA, means that the component nucleotides were assembled in vitro. Manual chemical synthesis of DNA may be accomplished using well established procedures, or automated chemical synthesis can be performed using one of a number of commercially available machines.

Stringent conditions are sequence dependent and will be different in different circumstances. Generally, stringent conditions are selected to be about 5° C. lower than the thermal melting point (Tm) for the specific sequence at a defined ionic strength and pH. The Tm is the temperature (under defined ionic strength and pH) at which 50% of the target sequence hybridizes to a perfectly matched probe. Appropriate stringent conditions are known to those skilled in the art or can be found in Current Protocols in Molecular Biology, John Wiley & Sons, N.Y. (1989), 6.3.1-6.3.6 (incorporated herein by reference). For the purposes of this disclosure, stringent conditions include at least one wash (usually 2) in 0.2×SSC at a temperature of at least about 50° C., usually about 55° C., for 20 minutes, or equivalent conditions.

The hybridization portion of the two hybridizing nucleic acids is usually at least 40 nucleotides in length, more usually at least about 75 nucleotides in length, more particularly at least 100 nucleotides in lengths. The hybridizing portion of the hybridizing nucleic acid is at least 80%, at least 90%, or at least 98% identical to SEQ ID NO:1.

Another aspect of the present invention relates to an isolated nucleic acid molecule comprising one or more open reading frames listed in Table 1 of the US Patent Application Publication No. 20110167520 A1, which is incorporated herein by reference in its entirety. An "open reading frame" (ORF) is a region of a nucleotide sequence which encodes a polypeptide. This region may represent a portion of a coding sequence or a total coding sequence. The table sets forth a list of open reading frames identified in the isolated nucleic acid molecules, wherein the open reading frames encode *Xenorhabdus* proteins or polypeptide or fragments thereof which are homologues of known proteins or unknown proteins, or of tRNA's or rRNA's or fragments thereof which are homologues of known tRNA's or rRNA's.

Open reading frames in genomic sequences can be screened for the presence of protein homologues utilizing one or a number of different search algorithms that have been developed, one example of which are the suite of programs referred to as BLAST programs. There are five implementations of BLAST, three designed for nucleotide sequences queries (BLASTN, BLASTX, and TBLASTX) and two designed for protein sequence queries (BLASTP and TBLASTN) (Coulson, Trends in Biotechnology 12:76-80 (1994); Birren et al., Genome Analysis 1:543-559 (1997)). Other examples of suitable programs that can be utilized are well known in the art. In addition, unidentified reading frames may be screened for by gene prediction software such as GenScan, which is located at http://gnomic.stanford.edu/GENSCANW.html. Novel genes, i.e., with no known homologs, can be predicted with the program GeneMark, which calculates the probability of a gene based on the presence of a gene-like 'grammar' in the DNA sequence (i.e., start and stop signals, and a significant open reading frame) and statistical analyses of protein-coding potential through biases in putative codon usage (see http://genemark.biology.gatech.edu/GeneMark for details).

The present invention also provides an isolated nucleic acid molecule comprising a nucleotide sequence, wherein: (1) the nucleotide sequence hybridizes under stringent conditions to a second isolated nucleic acid molecule, wherein the hybridizing portion of the nucleotide sequence of the second isolated nucleic acid molecule encodes a polypeptide or protein having an amino acid sequence of SEQ ID NO:2; (2) the nucleotide sequence encodes a polypeptide or protein, wherein the amino acid sequence of the polypeptide or protein is substantially identical to SEQ ID NO:2; or (3) the nucleotide sequence is the complement of (1) or (2).

In one embodiment, an isolated nucleic acid molecule comprises a nucleotide sequence, wherein the nucleotide sequence encodes a polypeptide or protein having an amino acid sequence that is substantially identical to SEQ ID NO:2.

The term "polypeptide" or "protein" refers to a linear polymer composed of amino acids connected by peptide bonds.

By "substantial identical" or "substantially identical" as used in reference to two amino acid sequences, it is meant that one amino acid sequence is identical to the other amino acid sequence or has at least 50% sequence identity, at least 70% sequence identity, preferably at least 80%, more preferably at least 90%, and most preferably at least 95% identity when compared to the other amino acid sequence as a reference sequence using the programs described herein; preferably BLAST using standard parameters, as described below.

"Percentage of sequence identity" is determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

Polypeptides which are "substantially similar" share sequences as noted above except that residue positions which are not identical may differ by conservative amino acid changes. Conservative amino acid substitutions refer to the interchangeability of residues having similar side chains. "Conservative amino acid substitutions" refer to substitutions of one or more amino acids in a native amino acid sequence with another amino acid(s) having similar side chains, resulting in a silent change. Conserved substitutes for an amino acid within a native amino acid sequence can be selected from other members of the group to which the naturally occurring amino acid belongs. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine, valine-isoleucine, phenylalanine-tyrosine, lysine-arginine, alanine-valine, aspartic acid-glutamic acid, and asparagine-glutamine.

Optimal alignment of sequences for comparison can use any means to analyze sequence identity (homology) known in the art, e.g., by the progressive alignment method of termed "PILEUP" (Morrison, Mol. Biol. Evol. 14:428-441 (1997), as an example of the use of PILEUP); by the local homology algorithm of Smith & Waterman (Adv. Appl. Math. 2: 482 (1981)); by the homology alignment algorithm of Needleman & Wunsch (J. Mol. Biol. 48:443 (1970)); by the search for similarity method of Pearson (Proc. Natl. Acad. Sci. USA 85: 2444 (1988)); by computerized implementations of these algorithms (e.g., GAP, BESTFIT, FASTA, and TFASTA in the Wisconsin Genetics Software Package, Genetics Computer Group, 575 Science Dr., Madison, Wis.); ClustalW (CLUSTAL in the PC/Gene program by Intelligenetics, Mountain View, Calif., described by, e.g., Higgins, Gene 73: 237-244 (1988); Corpet, Nucleic Acids Res. 16:10881-10890 (1988); Huang, Computer Applications in the Biosciences 8:155-165 (1992); and Pearson, Methods in Mol. Biol. 24:307-331 (1994); Pfam (Sonnhammer, Nucleic Acids Res. 26:322-325 (1998); TreeAlign (Hein, Methods Mol. Biol. 25:349-364 (1994); MES-ALIGN, and SAM sequence alignment computer programs; or, by manual visual inspection.

Another example of algorithm that is suitable for determining sequence similarity is the BLAST algorithm, which is described in Altschul et al, J. Mol. Biol. 215: 403-410 (1990). Software for performing BLAST analyses is publicly available through the National Center for Biotechnology Information (NCBI), http://www.ncbi.nlm.nih.gov/; see also Zhang, Genome Res. 7:649-656 (1997) for the "PowerBLAST" variation. This algorithm involves first identifying high scoring sequence pairs (HSPs) by identifying short words of length W in the query sequence that either match or satisfy some positive valued threshold score T when aligned with a word of the same length in a database sequence. T is referred to as the neighborhood word score threshold (Altschul et al, J. Mol. Biol. 215: 403-410 (1990)). These initial neighborhood word hits act as seeds for initiating searches to find longer HSPs containing them. The word hits are extended in both directions along each sequence for as far as the cumulative alignment score can be increased. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment. The BLAST program uses as defaults a wordlength (W) of 11, the BLOSUM62 scoring matrix (see Henikoff, Proc. Natl. Acad. Sci. USA 89:10915-10919 (1992)) alignments (B) of 50, expectation (E) of 10, M=5, N=−4, and a comparison of both strands. The term BLAST refers to the BLAST algorithm which performs a statistical analysis of the similarity between two sequences; see, e.g., Karlin, Proc. Natl. Acad. Sci. USA 90:5873-5787 (1993). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001.

One skilled in the art will recognize that these values of sequence identity can be appropriately adjusted to determine corresponding sequence identity of two nucleotide sequences encoding the proteins of the present invention by taking into account codon degeneracy, conservative amino acid substitutions, reading frame positioning and the like. Substantial identity of nucleotide sequences for these purposes normally means sequence identity of at least 40%, preferably at least 60%, more preferably at least 90%, and most preferably at least 95%.

The term "codon degeneracy" refers to divergence in the genetic code permitting variation of the nucleotide sequence without effecting the amino acid sequence of an encoded polypeptide. The skilled artisan is well aware of the "codon-bias" exhibited by a specific host cell in usage of nucleotide codons to specify a given amino acid. Therefore, when synthesizing a gene for expression in a host cell, it is desirable to design the gene such that its frequency of codon usage approaches the frequency of preferred codon usage of the host cell.

The present invention also includes an isolated nucleic acid comprising a nucleotide sequence encoding a polypeptide having an amino acid sequence as set forth in SEQ ID NO:2 with conservative amino acid substitutions.

In a preferred embodiment of the present invention, the isolated nucleic acid molecule comprising a nucleotide sequence encodes an insect inhibitory protein, wherein the nucleotide sequence is SEQ ID NO:1. The term "insect inhibitory protein" refers to any polypeptide or protein or a substantial portion thereof that exhibits insect inhibitory activity, wherein said activity is manifested by inhibiting the growth or development of, or contributing substantially to, or causing the death of a Coleopteran, a Dipteran, a Lepidopteran, a Hemipteran, a Hymenopteran, or a sucking and piercing insect or insect larvae thereof. For instance, the present invention provides an isolated nucleic acid molecule comprising a nucleotide sequence encoding all or substantial portion of a polypeptide having an amino acid sequence substantially identical to SEQ ID NO:2.

The term "insect inhibitory protein" also refers to any polypeptide or protein with modified amino acid sequence, such as sequence which has been mutated, truncated, increased and the like and which maintains at least the insect inhibitory activity associated with the native protein. Accordingly, the isolated nucleic acids encoding those polypeptide or protein with such modification are also within the scope of the present invention.

Another aspect of the present invention relates to a class of isolated nucleic acid molecules comprising promoter sequences or regulatory elements, particularly those found within SEQ ID NO:1 or the complement thereof.

The term "promoter sequence" means a nucleotide sequence that is capable of, when located in cis to a structural nucleotide sequence encoding a polypeptide or protein, functioning in a way that directs expression of one or more mRNA molecules that encodes the polypeptide or protein. Such promoter regions are typically found upstream of the trinucleotide ATG sequence at the start site of a protein coding region. Promoter sequences can also include sequences from which transcription of transfer RNA (tRNA) or ribosomal RNA (rRNA) sequences are initiated. Transcription involves the synthesis of an RNA chain representing one strand of a DNA duplex. By "representing" it is meant that the RNA is identical in sequence with one strand of the DNA; it is complementary to the other DNA strand, which provides the template for its synthesis. Transcription takes place by the usual process of complementary base pairing, catalyzed and scrutinized by the enzyme RNA polymerase. The reaction can be divided into three stages described as initiation, elongation and termination. Initiation begins with the binding of RNA polymerase to the double stranded (DS or ds) DNA. The sequence of DNA required for the initiation reaction defines the promoter. The site at which the first nucleotide is incorporated is called the startsite or startpoint of transcription. Elongation describes the phase during which the enzyme moves along the DNA and extends the growing RNA chain. Elongation involves the disruption of the DNA double stranded structure in which a transiently unwound region exists as a hybrid RNA-DNA duplex and a displaced single strand of DNA. Termination involves recognition of the point at which no further bases should be added to the chain. To terminate transcription, the formation of phosphodiester bonds must cease and the transcription complex must come apart. When the last base is added to the RNA chain, the RNA-DNA hybrid is disrupted, the DNA reforms into a duplex state, and the RNA polymerase enzyme and RNA molecule are both released from the DNA. The sequence of DNA required for the termination reaction is called the terminator.

Generally, for bacteria the optimal promoter is a sequence consisting of a −35 hexamer separated by about 17 base pairs from a −10 hexamer and lies from about 7 to about 10 base pairs upstream of the startpoint of transcription, but these sequences can vary among and between sequences which are recognized by the RNA polymerase. The startpoint of transcription generally lies from about 20 to about 50 base pairs upstream of the startpoint of translation of one or more open reading frames which comprise the entire length of an mRNA transcript. Some promoters can be recognized by RNA polymerase alone and in these cases, an accessible promoter will always be transcribed. Promoter availability may be determined by extraneous proteins, which either may act directly at the promoter to block access by RNA polymerase, or may function indirectly by controlling the structure of the genome in the region. Other promoters are not by themselves adequate to support transcription initiation and thus ancillary protein and or RNA factors are required to further initiation. The additional protein or RNA factors usually act by recognizing sequences of DNA that are close to, or overlap with, the sequence bound by RNA polymerase itself. Additionally, some of these ancillary factors must touch and concern the RNA polymerase in order to effect efficient transcription initiation as well as transcription elongation.

Promoters of the present invention can be included within sequences up to 10 kb upstream of the trinucleotide ATG sequence at the start site of a protein coding region, tRNA, or rRNA. Promoters of the present invention can preferably be included within sequences up to 5 kb upstream of the trinucleotide ATG sequence at the start site of a protein coding region, tRNA or rRNA. Promoters of the present invention can more preferably be included within sequences up to 2 kb upstream of the trinucleotide ATG sequence at the start site of a protein coding region, tRNA or rRNA. Promoters of the present invention can most preferably be included within sequences up to 500 bp upstream of the trinucleotide ATG sequence at the start site of a protein, tRNA, or rRNA coding region. While in many circumstances a 300 bp promoter may be sufficient for expression, additional sequences may act to further regulate expression, for example, in response to biochemical, developmental or environmental signals. In a preferred embodiment of the present invention, the promoter is upstream of an nucleic acid sequence that encodes a *Xenorhabdus* protein or fragment thereof.

The term "regulatory element" is intended to mean a series of nucleotides that determines if, when, and at what level a particular gene is expressed. Regulatory DNA sequences specifically interact with regulatory or other proteins. Many regulatory elements act in cis ("cis elements") and are believed to affect DNA topology, producing local conformations that selectively allow or restrict access of RNA polymerase to the DNA template or that facilitate selective opening of the double helix at the site of transcriptional initiation, i.e., the transcriptional startsite referred to above. Cis elements occur within, near to, adjacent to, or at a distance from a particular promoter, but remain linked to the promoter sequence along the sequence of phosphodiester bonds which comprise the nucleotide sequence within which the promoter resides. Cis elements are not limited to promoters, but may be imparted to RNA sequences derived from transcription from DNA sequences of the present invention, wherein such RNA cis elements are involved in post transcriptional regulation of gene expression. For example, elements which are known as inverted repeat sequences can assist in the formation of hairpin structures which prevent, inhibit, or otherwise modulate the translational efficiency of the RNA sequence, or which regulate the survival of the RNA sequence. Other elements may function to bind ribosomes or components which enhance or suppress translational efficiency. Cis elements can be identified using known cis elements as a target sequence or target motif in the BLAST. Promoters of the present invention include homologues of cis elements known to effect gene regulation that show homology with the nucleic acid molecules of the present invention.

The isolated nucleic acid molecules of the present invention also include nucleic acid molecules that encode ribosomal RNA (rRNA), transfer RNA (tRNA) molecules, or other nucleic acid molecules which function to regulate gene expression, transcription, translation by acting alone or in combination with other cellular components in activating, inhibiting, terminating or anti-terminating gene expression functions, or by acting alone or in combination with other structural molecules to form or assist in the formation of said structural molecules.

A "substantial portion" of a nucleotide sequence comprises enough of the sequence to afford specific identification and/or isolation of a nucleic acid fragment comprising the sequence. In general, gene specific oligonucleotide probes comprising 20-30 contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12-15 bases may be used as amplification primers in PCR in order to obtain a particular nucleic acid fragment comprising the primers. The skilled artisan, having the benefit of the sequences as reported herein, may now use all or a substantial portion of the disclosed sequences for purposes known to those skilled in this art. Accordingly, the instant invention comprises the complete sequences as reported in the accompanying Sequence Listing, as well as substantial portions of those sequences as defined above.

It is also contemplated by the inventors that the isolated nucleic acid molecules of the present invention also include known types of modifications, for example, labels which are known in the art, methylation, "caps", substitution of one or more of the naturally occurring nucleotides with an analog. Other known modifications include internucleotide modifications, for example, those with uncharged linkages (methyl phosphonates, phosphotriesters, phosphoamidates, carbamates, etc.) and with charged linkages (phosphorothioates, phosphorodithioates, etc.), those containing pendant moieties, such as, proteins (including nucleases, metabolic toxins, antibodies, signal peptides, poly-L-lysine, etc.), those with intercalators (acridine, psoralen, etc.), those containing chelators (metals, radioactive metals, boron, oxidative metals, etc.), those containing alkylators, and those with modified linkages (alpha anomeric nucleic acids, etc.).

The nucleic acids of the present invention may be used to isolate nucleic acids encoding homologous proteins from the same or other species. Isolation of homologous genes using sequence-dependent protocols is well known in the art. Examples of sequence-dependent protocols include, but are not limited to, methods of nucleic acid hybridization, and methods of DNA and RNA amplification as exemplified by various uses of nucleic acid amplification technologies (e.g., polymerase chain reaction, ligase chain reaction).

For example, genes encoding homologous proteins, either as cDNAs or genomic DNAs, could be isolated directly by using all or a portion of the nucleic acids of the present invention as DNA hybridization probes to screen cDNA or genomic libraries from any desired organism employing methodology well known to those skilled in the art. Methods for forming such libraries are well known in the art. Specific oligonucleotide probes based upon the nucleic acids of the present invention can be designed and synthesized by methods known in the art. Moreover, the entire sequences of the nucleic acids can be used directly to synthesize DNA probes by methods known to the skilled artisan such as random primer DNA labeling, nick translation, or end-labeling techniques, or RNA probes using available in vitro transcription systems. In addition, specific primers can be designed and used to amplify a part or all of the sequences. The resulting amplification products can be labeled directly during amplification reactions or labeled after amplification reactions, and used as probes to isolate full length cDNA or genomic DNAs under conditions of appropriate stringency.

Alternatively, the nucleic acids of interest can be amplified from nucleic acid samples using amplification techniques. For instance, the disclosed nucleic acids may be used to define a pair of primers that can be used with the polymerase chain reaction (Mullis, et al., Cold Spring Harbor Symp. Quant. Biol. 51:263-273 (1986); Erlich et al., EP 50,424; EP 84,796, EP 258,017, EP 237,362; Mullis, EP 201,184; Mullis et al., U.S. Pat. No. 4,683,202; Erlich, U.S. Pat. No. 4,582,788; and Saiki, R. et al., U.S. Pat. No. 4,683,194) to amplify and obtain any desired nucleic acid or fragment directly from mRNA, from cDNA, from genomic libraries or cDNA libraries. PCR and other in vitro amplification methods may also be useful, for example, to clone nucleic acid sequences that code for proteins to be expressed, to make nucleic acids to use as probes for detecting the presence of the desired mRNA in samples, for nucleic acid sequencing, or for other purposes.

In addition, two short segments of the nucleic acids of the present invention may be used in polymerase chain reaction protocols, for example, the RACE protocol (Frohman et al., Proc. Natl. Acad. Sci. USA 85:8998 (1988)), to amplify longer nucleic acids encoding homologous genes from DNA or RNA from other sources.

Nucleic acids of interest may also be synthesized, either completely or in part, especially where it is desirable to provide plant-preferred sequences, by well-known techniques as described in the technical literature. See, e.g., Carruthers et al., Cold Spring Harbor Symp. Quant. Biol. 47:411-418 (1982), and Adams et al., J. Am. Chem. Soc. 105:661 (1983). Thus, all or a portion of the nucleic acids of the present invention may be synthesized using codons preferred by a selected plant host. Plant-preferred codons may be determined, for example, from the codons used most frequently in the proteins expressed in a particular plant host species. Other modifications of the gene sequences may result in mutants having slightly altered activity.

Availability of the nucleotide sequences encoding *Xenorhabdus* proteins facilitates immunological screening of DNA expression libraries. Synthetic polypeptides representing portions of the amino acid sequences of *Xenorhabdus* proteins may be synthesized. These polypeptides can be used to immunize animals to produce polyclonal or monoclonal antibodies with specificity for polypeptides or proteins comprising the amino acid sequences. These antibodies can be then be used to screen expression libraries to isolate genes of interest (Lemer, Adv. Immunol. 36: 1 (1984); Sambrook et al., Molecular Cloning: A Laboratory Manual; Cold Spring Harbor Laboratory Press: Cold Spring Harbor, (1989)). It is understood that people skilled in the art are familiar with the standard resource materials which describe specific conditions and procedures for the construction, manipulation and isolation of antibodies (see, for example, Harlow and Lane, In Antibodies: A Laboratory Manual, Cold Spring Harbor Press, Cold Spring Harbor, N.Y. (1988)).

Another aspect of the present invention relates to a method for obtaining a nucleic acid comprising a nucleotide sequence encoding a *Xenorhabdus* protein homologue having an amino acid sequence at least 70% identical to SEQ ID NO:2. In a preferred embodiment, the method of the present invention for obtaining a nucleic acid encoding all or a substantial portion of the amino acid sequence of a *Xenorhabdus* protein homologue comprising: (a) probing an expression library with a hybridization probe comprising a nucleotide sequence encoding a polypeptide having an amino acid sequence set forth in SEQ ID NO:2; or an amino acid sequence set forth in SEQ ID NO:2 with conservative amino acid substitutions; (b) identifying a DNA clone that hybridizes to the hybridization probe; (c) isolating the DNA clone identified in step (b); and (d) sequencing the DNA fragment that comprises the clone isolated in step (c) wherein the sequenced nucleic acid molecule encodes all or a substantial portion of the amino acid sequence of the *Xenorhabdus* protein homologue.

In another preferred embodiment, the method of the present invention for obtaining a nucleic acid fragment encoding a substantial portion of an amino acid sequence of a *Xenorhabdus* protein homologue comprising: (a) synthesizing a first and a second oligonucleotide primers corresponding to a portion of the coding sequence of a second nucleic acid molecule set forth in SEQ ID NO:1; and (b) amplifying a DNA insert present in a cloning vector using the first and second oligonucleotide primers of step (a) wherein the amplified nucleic acid molecule encodes all or a substantial portion of the amino acid sequence of the *Xenorhabdus* protein homologue.

Protein and Polypeptide Molecules

The present invention, in another aspect, provides a substantially purified protein or polypeptide molecule comprising an amino acid sequence, wherein the amino acid sequence is defined as follows: (1) the amino acid sequence is encoded by a first nucleotide sequence which specifically hybridizes to the complement of a second nucleotide sequence set forth in SEQ ID NO:1; (2) the amino acid sequence is encoded by a third nucleotide sequence that is at least 50% identical to all or a substantial portion of a coding sequence located within SEQ ID NO:1; or (3) the amino acid sequence is substantially identical to SEQ ID NO:2. In alternative embodiments, the third nucleotide sequence is at least 55% identical, at least 60% identical, at least 65% identical, at least 70% identical, at least 75% identical, at least 80% identical, at least 85% identical, at least 90% identical, at least 95% identical to all or a substantial portion of a coding sequence located within SEQ ID NO:1. In a preferred embodiment, the third nucleotide sequence is 100% identical to all or a substantial portion of a coding sequence located within SEQ ID NO:1. In a preferred embodiment, the amino acid sequence is at least 60% identical, at least 70% identical, at least 80% identical, at least 90% identical, at least 95% identical, at least 98% identical to SEQ ID NO:2.

The term "substantially purified protein or polypeptide molecule" refers to a protein or polypeptide molecule separated from substantially all other molecules normally associated with it in its native state. More preferably a substantially purified protein or polypeptide molecule is the predominant species present in a preparation. A substantially purified molecule may be greater than 60% free, preferably 75% free, more preferably 90% free, and most preferably 95% free from the other molecules (exclusive of solvent) present in the natural mixture.

It is well known in the art that proteins or polypeptides may undergo modification, including post-translational modifications, such as, but not limited to, disulfide bond formation, glycosylation, phosphorylation, or oligomerization. Thus, as used herein, the term "protein molecule" or "polypeptide molecule" includes any protein molecule that is modified by any biological or non-biological process. The terms "amino acid" and "amino acids" refer to all naturally occurring L-amino acids. This definition is meant to include norleucine, ornithine, homocysteine, and homoserine.

The polypeptides or proteins of the present invention may be produced via chemical synthesis, or more preferably, by expression in a suitable bacterial or eukaryotic host. Suitable methods for expression are described by Sambrook, et al., (In: Molecular Cloning, A Laboratory Manual, 2nd Edition, Cold Spring Harbor Press, Cold Spring Harbor, N.Y. (1989)), or similar texts.

The polypeptides or protein molecule of the present invention may also include fusion protein or polypeptide molecules. A protein or polypeptide molecule that comprises one or more additional polypeptide regions not derived from that protein molecule is a "fusion" protein or polypeptide molecule. Such molecules may be derivatized to contain carbohydrate or other moieties (such as keyhole limpet hemocyanin, etc.). Fusion protein or polypeptide molecules of the present invention are preferably produced via recombinant means.

The protein or polypeptide molecules of the present invention may also include protein or polypeptide molecules encoded by all or a substantial portion of protein-encoding sequences in SEQ ID NO:1 or complements thereof or, fragments or fusions thereof in which conservative, non-essential, or not relevant, amino acid residues have been added, replaced, or deleted. An example of such a homologue is the homologue protein from different strains or species. Such a homologue can be obtained by any of a variety of methods. For example, as indicated above, one or more of the disclosed sequences (all or a substantial portion of the protein-encoding sequence of SEQ ID NO:1 or complements thereof) will be used to define a pair of primers that may be used to isolate the homologue-encoding nucleic acid molecules from any desired species. Such molecules can be expressed to yield homologues by recombinant means.

Antibodies

Another aspect of the present invention concerns antibodies, single-chain antigen binding molecules, or other proteins that specifically bind to one or more of the protein or polypeptide molecules of the present invention and their homologues, fusions or fragments. Such antibodies may be used to quantitatively or qualitatively detect the protein or polypeptide molecules of the present invention. As used herein, an antibody or polypeptide is said to "specifically bind" to a protein or polypeptide molecule of the present invention if such binding is not competitively inhibited by the presence of non-related molecules. In a preferred embodiment the antibodies of the present invention bind to protein or polypeptide molecules of the present invention, in a more preferred embodiment of the antibodies of the present invention bind to protein or polypeptide molecules derived from *Xenorhabdus*.

Nucleic acid molecules that encode all or part of the protein or polypeptide of the present invention can be expressed, via recombinant means, to yield protein or polypeptides that can in turn be used to elicit antibodies that are capable of binding the expressed protein or polypeptide. Such antibodies may be used in immunoassays for that protein or polypeptide. Such protein or polypeptide-encoding molecules, or their fragments may be "fusion" molecules (i.e., a part of a larger nucleic acid molecule) such that, upon expression, a fusion protein is produced. It may be desirable to derivatize the obtained antibodies, for example with a ligand group (such as biotin) or a detectable marker group (such as a fluorescent group, a radioisotope or an enzyme). Such antibodies may be used in immunoassays for that protein. In a preferred embodiment, such antibodies can be used to screen DNA expression libraries to isolate clones containing full-length insert of genes (Lerner, Adv. Immunol. 36: 1 (1984); Sambrook et al., Molecular Cloning: A Laboratory Manual; Cold Spring Harbor Laboratory Press: Cold Spring Harbor, (1989)).

The antibodies that specifically bind proteins and protein fragments of the present invention may be polyclonal or monoclonal, and may comprise intact immunoglobulins, or antigen binding portions of immunoglobulins (such as (F(ab'), F(ab')2 fragments), or single-chain immunoglobulins producible, for example, via recombinant means). It is understood that practitioners are familiar with the standard resource materials which describe specific conditions and procedures for the construction, manipulation and isolation of antibodies (see, for example, Harlow and Lane, Antibodies: A Laboratory Manual, Cold Spring Harbor Press, Cold Spring Harbor, N.Y. (1988)).

In a preferred embodiment, the antibodies of the present invention specifically bind to one or more of the insect inhibitory polypeptides or proteins of the present invention. Such antibodies may be used to detect the presence of such insect inhibitory polypeptides or proteins in a sample.

The present invention also provide a method for detecting an insect inhibitory polypeptide or protein in a biological sample, the method generally comprising: (1) obtaining a biological sample; (2) contacting the sample with an antibody that specifically binds to the polypeptide or protein, under conditions effective to allow the formation of complexes; and (3) detecting the complexes so formed.

Plant Constructs and Plant Transformants

The present invention also relates to a plant recombinant vector or construct comprising a structural nucleotide sequence encoding a *Xenorhabdus* protein or polypeptide. In a preferred embodiment, a plant recombinant vector or construct of the present invention comprises a structural nucleotide sequence encoding an insect inhibitory protein or polypeptide of the present invention. The present invention also relates to a transformed plant cell or plant comprising in its genome an exogenous nucleic acid encoding one or more *Xenorhabdus* or *Photorhabdus* proteins or polypeptides of the present invention. The present invention also relates to methods for creating a transgenic plant in which one or more *Xenorhabdus* or *Photorhabdus* proteins or polypeptides of the present invention are overexpressed.

By "exogenous" it is meant that a nucleic acid originates from outside the plant. An exogenous nucleic acid can have a naturally occurring or non-naturally occurring nucleotide sequence. One skilled in the art understands that an exogenous nucleic acid can be a heterologous nucleic acid derived from a different plant species than the plant into which the nucleic acid is introduced or can be a nucleic acid derived from the same plant species as the plant into which it is introduced.

The term "overexpression" refers to the expression of a polypeptide or protein encoded by an exogenous nucleic acid introduced into a host cell, wherein said polypeptide or protein is either not normally present in the host cell, or wherein said polypeptide or protein is present in said host cell at a higher level than that normally expressed from the endogenous gene encoding said polypeptide or protein. By "endogenous gene" refers to a native gene in its natural location in the genome of an organism.

The term "genome" as it applies to plant cells encompasses not only chromosomal DNA found within the nucleus, but organelle DNA found within subcellular components of the cell. DNAs of the present invention introduced into plant cells can therefore be either chromosomally integrated or organelle-localized. The term "genome" as it applies to bacteria encompasses both the chromosome and plasmids within a bacterial host cell. Encoding DNAs of the present invention introduced into bacterial host cells can therefore be either chromosomally integrated or plasmid-localized.

Method which are well known to those skilled in the art may be used to construct the plant recombinant construct or vector of the present invention. These method include in vitro recombinant DNA techniques, synthetic techniques, and in vivo genetic recombination. Such techniques are described in Sambrook et al., Molecular Cloning, A Laboratory Manual, Cold Spring Harbor Press, Plainview, N.Y. (1989); and Ausubel et al., Current Protocols in Molecular Biology, John Wiley & Sons, New York, N.Y. (1989).

A plant recombinant construct or vector of the present invention contains a structural nucleotide sequence encoding one or more *Xenorhabdus* or *Photorhabdus* proteins or polypeptides of the present invention and operably linked regulatory sequences or control elements.

The term "operably linked", as used in reference to a regulatory sequence and a structural nucleotide sequence, means that the regulatory sequence causes regulated expression of the operably linked structural nucleotide sequence. "Expression" refers to the transcription and stable accumulation of sense or antisense RNA derived from the nucleic acid of the present invention. Expression may also refer to translation of mRNA into a polypeptide or protein. "Sense" RNA refers to RNA transcript that includes the mRNA and so can be translated into protein by the cell. "Antisense RNA" refers to a RNA transcript that is complementary to all or part of a target primary transcript or mRNA and that blocks the expression of a target gene (U.S. Pat. No. 5,107,065, incorporated herein by reference). The complementarity of an antisense RNA may be with any part of the specific gene transcript, i.e., at the 5' non-coding sequence, 3' non-translated sequence, introns, or the coding sequence. "RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from post-transcriptional processing of the primary transcript and is referred to as the mature RNA.

"Regulatory sequences" or "control elements" refer to nucleotide sequences located upstream (5' noncoding sequences), within, or downstream (3' non-translated sequences) of a structural nucleotide sequence, and which influence the transcription, RNA processing or stability, or translation of the associated structural nucleotide sequence. Regulatory sequences may include promoters, translation leader sequences, introns, and polyadenylation recognition sequences.

The promoter sequence may consist of proximal and more distal upstream elements, the latter elements often referred to as enhancers. Accordingly, an "enhancer" is a DNA sequence which can stimulate promoter activity and may be an innate element of the promoter or a heterologous element inserted to enhance the level or tissue-specificity of a promoter. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental conditions.

Promoters which are known or are found to cause transcription of DNA in plant cells can be used in the present invention. Such promoters may be obtained from a variety of sources such as plants and plant viruses. A number of promoters, including constitutive promoters, inducible promoters and tissue-specific promoters, that are active in plant cells have been described in the literature. It is preferred that the particular promoter selected should be capable of causing sufficient expression to result in the production of an effective amount of a protein to cause the desired phenotype. In addition to promoters that are known to cause transcription of DNA in plant cells, other promoters may be identified for use in the current invention by screening a plant cDNA library for genes that are selectively or preferably expressed in the target tissues and then determine the promoter regions.

The term "constitutive promoter" means a regulatory sequence which causes expression of a structural nucleotide sequence in most cells or tissues at most times. Constitutive promoters are active under most environmental conditions and states of development or cell differentiation. A variety of constitutive promoters are well known in the art. Examples of constitutive promoters that are active in plant cells include but are not limited to the nopaline synthase (NOS) promoters; the cauliflower mosaic virus (CaMV) 19S and 35S; the tobacco mosaic virus promoter; the figwort mosaic virus promoters; and actin promoters, such as the *Arabidopsis* actin gene promoter (see, e.g., Huang, Plant Mol. Biol. 33:125-139 (1997)).

The term "inducible promoter" refers to a regulatory sequence which causes conditional expression of a structural nucleotide sequence under the influence of changing environmental conditions or developmental conditions. Examples of inducible promoters include but are not limited to the light-inducible promoter from the small subunit of ribulose-1,5-bis-phosphate carboxylase (ssRUBISCO); the drought-inducible promoter of maize (Busk, Plant J. 11:1285-1295 (1997)); the cold, drought, and high salt inducible promoter from potato (Kirch, Plant Mol. Biol. 33:897-909 (1997)); a nitrate-inducible promoter derived from the spinach nitrite reductase gene (Back et al., Plant Mol. Biol. 17:9 (1991)); salicylic acid inducible promoter (Uknes et al., Plant Cell 5:159-169 (1993); Bi et al., Plant J. 8:235-245 (1995)); the auxin-response elements El promoter fragment (AuxREs) in the soybean (*Glycine max* L.) (Liu, Plant Physiol. 115:397-407 (1997)); the auxin-responsive *Arabidopsis* GST6 promoter (also responsive to salicylic acid and hydrogen peroxide) (Chen, Plant J. 10: 955-966 (1996)); the auxin-inducible parC promoter from tobacco (Sakai, 37:906-913 (1996)); a plant biotin response element (Streit, Mol. Plant Microbe Interact. 10:933-937 (1997)); the promoter responsive to the stress hormone abscisic acid (Sheen, Science 274:1900-1902 (1996)); the maize In2-2 promoter activated by benzenesulfonamide herbicide safeners (De Veyl der, Plant Cell Physiol. 38:568-577 (1997)); a tetracycline-inducible promoter, such as the promoter for the *Avena sativa* L. (oat) arginine decarboxylase gene (Masgrau, Plant J. 11:465-473 (1997)); and a salicylic acid-responsive element (Stange, Plant J. 11:1315-1324 (1997)).

The term "tissue-specific promoter" means a regulatory sequence that causes transcriptions or enhanced transcriptions of DNA in specific cells or tissues at specific times during plant development, such as in vegetative tissues or reproductive tissues. Examples of tissue-specific promoters under developmental control include promoters that initiate transcription only (or primarily only) in certain tissues, such as vegetative tissues, e.g., roots, leaves or stems, or reproductive tissues, such as fruit, ovules, seeds, pollen, pistils, flowers, or any embryonic tissue. Reproductive tissue specific promoters may be, e.g., ovule-specific, embryo-specific, endosperm-specific, integument-specific, seed coat-specific, pollen-specific, petal-specific, sepal-specific, or some combination thereof. One of skill will recognize that a tissue-specific promoter may drive expression of operably linked sequences in tissues other than the target tissue. Thus, as used herein a tissue-specific promoter is one that drives expression preferentially in the target tissue, but may also lead to some expression in other tissues as well.

A variety of promoters specifically active in vegetative tissues, such as leaves, stems, roots and tubers, can also be used to express the nucleic acids of the invention. Examples of tuber-specific promoters include but are not limited to the class I and II patatin promoters (Bevan et al., EMBO J. 8: 1899-1906 (1986); Koster-Topfer et al., Mol Gen Genet. 219: 390-396 (1989); Mignery et al., Gene. 62: 27-44 (1988); Jefferson et al., Plant Mol. Biol. 14: 995-1006 (1990)), the promoter for the potato tuber ADPGPP genes, both the large and small subunits; the sucrose synthase promoter (Salanoubat and Belliard, Gene. 60: 47-56 (1987), Salanoubat and Belliard, Gene. 84: 181-185 (1989)); and the promoter for the major tuber proteins including the 22 kd protein complexes and proteinase inhibitors (Hannapel, Plant Physiol. 101: 703-704 (1993)). Examples of leaf-specific promoters include but are not limited to the ribulose biphosphate carboxylase (RBCS or RuBISCO) promoters (see, e.g., Matsuoka, Plant J. 6:311-319 (1994)); the light harvesting chlorophyll a/b binding protein gene promoter (see, e.g., Shiina, Plant Physiol. 115-0.477-483 (1997); Casal, Plant Physiol. 116:1533-1538 (1998)); and the *Arabidopsis thaliana* myb-related gene promoter (Atmyb5) (Li, FEBS Lett. 379:117-121 (1996)). Examples of root-specific promoter include but are not limited to the promoter for the acid chitinase gene (Samac et al., Plant Mol. Biol. 25: 587-596 (1994)); the root specific subdomains of the CaMV35S promoter that have been identified (Lam et al., Proc. Natl. Acad. Sci. (U.S.A.) 86:7890-7894 (1989)); the ORF13 promoter from *Agrobacterium rhizogenes* which exhibits high activity in roots (Hansen, Mol. Gen. Genet. 254:337-343 (1997)); the promoter for the tobacco root-specific gene TobRB7 (Yamamoto, Plant Cell 3:371-382 (1991)); and the root cell specific promoters reported by Conkling et al. (Conkling et al., Plant Physiol. 93:1203-1211 (1990)).

Another class of useful vegetative tissue-specific promoters are meristermatic (root tip and shoot apex) promoters. For example, the "SHOOTMERISTEMLESS" and "SCARECROW" promoters, which are active in the developing shoot or root apical meristems (Di Laurenzio, Cell 86:423-433 (1996); Long, Nature 379:66-69 (1996)), can be used. Another example of a useful promoter is that which controls the expression of 3-hydroxy-3-methylglutaryl coenzyme A reductase HMG2 gene, whose expression is restricted to meristematic and floral (secretory zone of the stigma, mature pollen grains, gynoecium vascular tissue, and fertilized ovules) tissues (see, e.g., Enjuto, Plant Cell. 7:517-527 (1995)). Also another example of a useful promoter is that which controls the expression of knl-related genes from maize and other species which show meristern-specific expression (see, e.g., Granger, Plant Mol. Biol. 31:373-378 (1996); Kerstetter, Plant Cell 6:1877-1887 (1994); Hake, Philos. Trans. R. Soc. Lond. B. Biol. Sci. 350:45-51 (1995). Another example of a meristematic promoter is the *Arabidopsis thaliana* KNAT1 promoter. In the shoot apex, KNAT1 transcript is localized primarily to the shoot apical meristem; the expression of KNATI in the shoot meristem decreases during the floral transition and is restricted to the cortex of the inflorescence stem (see, e.g., Lincoln, Plant Cell 6:1859-1876 (1994)).

Suitable seed-specific promoters can be derived from the following genes: MAC1 from maize (Sheridan, Genetics 142: 1009-1020 (1996); Cat3 from maize (GenBank No. L05934, Abler, Plant Mol. Biol. 22:10131-1038 (1993); vivparous-1 from *Arabidopsis* (Genbank No. U93215); Atimycl from *Arabidopsis* (Urao, Plant Mol. Biol. 32:571-57 (1996); Conceicao, Plant 5:493-505 (1994); napA from *Brassica napus* (GenBank No. J02798); the napin gene family from *Brassica napus* (Sjodahl, Planta 197:264-271 (1995)).

The ovule-specific BEL1 gene described in Reiser (1995) Cell 83:735-742, GenBank No. U39944, can also be used. See also Ray (1994) Proc. Natl. Acad. Sci. USA 91:5761-5765. The egg and central cell specific FIEEI promoter is also a useful reproductive tissue-specific promoter.

A maize pollen-specific promoter has been identified in maize (Guerrero (1990) Mol. Gen. Genet. 224:161-168). Other genes specifically expressed in pollen are described, e.g., by Wakeley (1998) Plant Mol. Biol. 37:187-192; Ficker (1998) Mol. Gen. Genet. 257:132-142; Kulikauskas (1997) Plant Mol. Biol. 34:809-814; Treacy (1997) Plant Mol. Biol. 34:603-611.

Promoters derived from genes encoding embryonic storage proteins, which includes the gene encoding the 2S storage protein from *Brassica napus* (Dasgupta, Gene 133:301-302 (1993); the 2 s seed storage protein gene family from *Arabidopsis*; the gene encoding oleosin 20 kD from *Brassica napus* (GenBank No. M63985); the genes encoding oleosin A (Genbank No. U09118) and oleosin B (Genbank No. U09119) from soybean; the gene encoding oleosin from *Arabidopsis* (Genbank No. Z17657); the gene encoding oleosin 18 kD from maize (GenBank No. J05212, Lee, Plant Mol. Biol. 26:1981-1987 (1994)); and the gene encoding low molecular weight sulphur rich protein from soybean (Choi, Mol Gen, Genet. 246:266-268 (1995)), can also be used.

Promoters derived from genes encoding for zein genes (including the 15 kD, 16 kD, 19 kD, 22 kD, 27 kD, and gamma genes) (Pedersen et al., Cell 29: 1015-1026 (1982)) can be also used. The zeins are a group of storage proteins found in maize endosperm.

Other promoters known to function, for example, in maize, include the promoters for the following genes: waxy, Brittle, Shrunken 2, Branching enzymes I and II, starch synthases, debranching enzymes, oleosins, glutelins, and sucrose synthases. A particularly preferred promoter for maize endosperm expression is the promoter for the glutelin gene from rice, more particularly the Osgt-1 promoter (Zheng et al., Mol. Cell Biol. 13: 5829-5842 (1993), herein incorporated by reference in its entirety). Examples of promoters suitable for expression in wheat include those promoters for the ADPglucose pyrophosphorylase (ADPGPP) subunits, the granule bound and other starch synthases, the branching and debranching enzymes, the embryogenesis-abundant proteins, the gliadins, and the glutenins Examples of such promoters in rice include those promoters for the ADPGPP subunits, the granule bound and other starch synthases, the branching enzymes, the debranching enzymes, sucrose synthases, and the glutelins. A particularly preferred promoter is the promoter for rice glutelin, Osgt-1. Examples of such promoters for barley include those for the ADPGPP subunits, the granule bound and other starch synthases, the branching enzymes, the debranching enzymes, sucrose synthases, the hordeins, the embryo globulins, and the aleuron specific proteins.

A tomato promoter active during fruit ripening, senescence and abscission of leaves and, to a lesser extent, of flowers can be used (Blume, Plant J. 12:731-746 (1997)). Other exemplary promoters include the pistol specific promoter in the potato (*Solarium tuberosum* L.) SK2 gene, encoding a pistil-specific basic endochitinase (Ficker, Plant Mol. Biol. 35:425-431 (1997)); the Blec4 gene from pea (*Pisum sativum* cv. Alaska), active in epidermal tissue of vegetative and floral shoot apices of transgenic alfalfa. This makes it a useful tool to target the expression of foreign genes to the epidermal layer of actively growing shoots. The tissue specific E8 promoter from tomato is also useful for directing gene expression in fruits.

It is recognized that additional promoters that may be utilized are described, for example, in U.S. Pat. Nos. 5,378,619, 5,391,725, 5,428,147, 5,447,858, 5,608,144, 5,608,144, 5,614,399, 5,633,441, 5,633,435, and 4,633,436, all of which are herein incorporated in their entirety. In addition, a tissue specific enhancer may be used (Fromm et al., The Plant Cell 1:977-984 (1989), herein incorporated by reference in its entirety). It is further recognized that since in most cases the exact boundaries of regulatory sequences have not been completely defined, DNA fragments of different lengths may have identical promoter activity.

The "translation leader sequence" refers to a DNA sequence located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency. Examples of translation leader sequences have been described (Turner, R. and Foster, G. D. (1995) Molecular Biotechnology 3:225).

The "3' non-translated sequences" refer to DNA sequences located downstream of a structural nucleotide sequence and include sequences encoding polyadenylation and other regulatory signals capable of affecting mRNA processing or gene expression. The polyadenylation signal functions in plants to cause the addition of polyadenylate nucleotides to the 3' end of the mRNA precursor. The polyadenylation sequence can be derived from the natural gene, from a variety of plant genes, or from T-DNA. An example of the polyadenylation sequence is the nopaline synthase 3' sequence (NOS 3'; Fraley et al., Proc. Natl. Acad. Sci. USA 80: 4803-4807 (1983)). The use of different 3' non-translated sequences is exemplified by Ingelbrecht et al., (1989) Plant Cell 1:671-680.

Generally, optimal expression in monocotyledonous and some dicotyledonous plants is obtained when an intron sequence is inserted between the promoter sequence and the structural gene sequence or, optionally, may be inserted in the structural coding sequence to provide an interrupted coding sequence. An example of such an intron sequence is the HSP 70 intron described in WO 93/19189.

A recombinant vector or construct of the present invention will typically comprise a selectable marker which confers a selectable phenotype on plant cells. Selectable markers may also be used to select for plants or plant cells that contain the exogenous nucleic acids encoding polypeptides or proteins of the present invention. The marker may encode biocide resistance, antibiotic resistance (e.g., kanamycin, G418 bleomycin, hygromycin, etc.), or herbicide resistance (e.g., glyphosate, etc.). Examples of selectable markers include, but are not limited to, a neo gene (Potrykus et al., Mol. Gen. Genet. 199:183-188 (1985)) which codes for kanamycin resistance and can be selected for using kanamycin, G418, etc.; a bar gene which codes for bialaphos resistance; a mutant EPSP synthase gene (Hinchee et al., Bio/Technology 6:915-922 (1988)) which encodes glyphosate resistance; a nitrilase gene which confers resistance to bromoxynil (Stalker et al., J. Biol. Chem. 263:6310-6314 (1988)); a mutant acetolactate synthase gene (ALS) which confers imidazolinone or sulphonylurea resistance (European Patent Application 154,204 (Sep. 11, 1985)); and a methotrexate resistant DHFR gene (Thillet et al., J. Biol. Chem. 263:12500-12508 (1988)).

A recombinant vector or construct of the present invention may also include a screenable marker. Screenable markers may be used to monitor expression. Exemplary screenable markers include a β-glucuronidase or uidA gene (GUS) which encodes an enzyme for which various chromogenic substrates are known (Jefferson, Plant Mol. Biol, Rep. 5:387-405 (1987); Jefferson et al., EMBO J. 6:3901-3907 (1987)); an R-locus gene, which encodes a product that regulates the production of anthocyanin pigments (red color) in plant tissues (Dellaporta et al., Stadler Symposium 11:263-282 (1988)); a β-lactamase gene (Sutcliffe et al., Proc. Natl. Acad. Sci. (U.S.A.) 75:3737-3741 (1978)), a gene which encodes an enzyme for which various chromogenic substrates are known (e.g., PADAC, a chromogenic cephalosporin); a luciferase gene (Ow et al., Science 234:856-859 (1986)) a xylE gene (Zukowsky et al., Proc. Natl. Acad. Sci. (U.S.A.) 80:1101-1105 (1983)) which encodes a catechol dioxygenase that can convert chromogenic catechols; an α-amylase gene (Ikatu et al., Bio/Technol. 8:241-242 (1990)); a tyrosinase gene (Katz et al., J. Gen. Microbiol. 129:2703-2714 (1983)) which encodes an enzyme capable of oxidizing tyrosine to DOPA and dopaquinone which in turn condenses to melanin; an α-galactosidase, which will turn a chromogenic α-galactose substrate.

Included within the terms "selectable or screenable marker genes" are also genes which encode a secretable marker whose secretion can be detected as a means of identifying or selecting for transformed cells. Examples include markers which encode a secretable antigen that can be identified by antibody interaction, or even secretable enzymes which can be detected catalytically. Secretable proteins fall into a number of classes, including small, diffusible proteins detectable, e.g., by ELISA, small active enzymes detectable in extracellular solution (e.g., α-amylase, β-lactamase, phosphinothricin transferase), or proteins which are inserted or trapped in the cell wall (such as proteins which include a leader sequence such as that found in the expression unit of extension or tobacco PR-S). Other possible selectable and/or screenable marker genes will be apparent to those of skill in the art.

In addition to a selectable marker, it may be desirous to use a reporter gene. In some instances a reporter gene may be used with or without a selectable marker. Reporter genes are genes which are typically not present in the recipient organism or tissue and typically encode for proteins resulting in some phenotypic change or enzymatic property. Examples of such genes are provided in K. Wising et al. Ann. Rev. Genetics, 22, 421 (1988), which is incorporated herein by reference. Preferred reporter genes include the beta-glucuronidase (GUS) of the uidA locus of E. coli, the chloramphenicol acetyl transferase gene from Tn9 of E. coli, the green fluorescent protein from the bioluminescent jellyfish Aequorea victoria, and the luciferase genes from firefly Photinus pyralis. An assay for detecting reporter gene expression may then be performed at a suitable time after said gene has been introduced into recipient cells. A preferred such assay entails the use of the gene encoding beta-glucuronidase (GUS) of the uidA locus of E. coli as described by Jefferson et al., (1987 Biochem. Soc. Trans. 15, 17-19) to identify transformed cells.

In preparing the DNA constructs of the present invention, the various components of the construct or fragments thereof will normally be inserted into a convenient cloning vector, e.g., a plasmid that is capable of replication in a bacterial host, e.g., E. coli. Numerous vectors exist that have been described in the literature, many of which are commercially available. After each cloning, the cloning vector with the desired insert may be isolated and subjected to further manipulation, such as restriction digestion, insertion of new fragments or nucleotides, ligation, deletion, mutation, resection, etc. so as to tailor the components of the desired sequence. Once the construct has been completed, it may then be transferred to an appropriate vector for further manipulation in accordance with the manner of transformation of the host cell.

A recombinant vector or construct of the present invention may also include a chloroplast transit peptide, in order to target the polypeptide or protein of the present invention to the plastid. The term "plastid" refers to the class of plant cell organelles that includes amyloplasts, chloroplasts, chromoplasts, elaioplasts, eoplasts, etioplasts, leucoplasts, and proplastids. These organelles are self-replicating, and contain what is commonly referred to as the "chloroplast genome," a circular DNA molecule that ranges in size from about 120 to about 217 kb, depending upon the plant species, and which usually contains an inverted repeat region. Many plastid-localized proteins are expressed from nuclear genes as precursors and are targeted to the plastid by a chloroplast transit peptide (CTP), which is removed during the import steps. Examples of such chloroplast proteins include the small subunit of ribulose-1,5-biphosphate carboxylase (ssRUBISCO, SSU), 5-enolpyruvateshikimate-3-phosphate synthase (EPSPS), ferredoxin, ferredoxin oxidoreductase, the light-harvesting-complex protein I and protein II, and thioredoxin F. It has been demonstrated that non-plastid proteins may be targeted to the chloroplast by use of protein fusions with a CTP and that a CTP sequence is sufficient to target a protein to the plastid. Those skilled in the art will also recognize that various other chimeric constructs can be made that utilize the functionality of a particular plastid transit peptide to import the enzyme into the plant cell plastid depending on the promoter tissue specificity.

The present invention also provide a transgenic plant comprising in its genome an isolated nucleic acid which comprises: (A) a 5' non-coding sequence which functions in the cell to cause the production of a mRNA molecule; which is linked to (B) a structural nucleotide sequence, wherein the structural nucleotide sequence encodes a Xenorhabdus protein or polypeptide of the present invention; which is linked to (C) a 3' non-translated sequence that functions in said cell to cause termination of transcription. In a preferred embodiment, the amino acid sequence of the above described polypeptide or protein is substantially identical to SEQ ID NO:2.

The term "transgenic plant" refers to a plant that contains an exogenous nucleic acid, which can be derived from the same plant species or from a different plant species. Transgenic plants of the present invention preferably have incorporated into their genome or transformed into their chloroplast or plastid genomes a selected polynucleotide (or "transgene"), that comprises at least a structural nucleotide sequence that encodes an insect inhibitory polypeptide having an amino acid sequence as set forth in SEQ ID NO:2. Transgenic plants are also meant to comprise progeny (descendant, offspring, etc.) of any generation of such a transgenic plant. A seed of any generation of all such transgenic insect-resistant plants wherein said seed comprises a DNA sequence encoding the polypeptide of the present invention is also an important aspect of the invention.

The DNA constructs of the present invention may be introduced into the genome of a desired plant host by a variety of conventional transformation techniques, which are well known to those skilled in the art. Preferred methods of transformation of plant cells or tissues are the Agrobacterium mediated transformation method and the biolistics or particle-gun mediated transformation method. Suitable plant transformation vectors for the purpose of Agrobacterium mediated transformation include those derived from a Ti plasmid of Agrobacterium tumefaciens, as well as those disclosed, e.g., by Herrera-Estrella et al., Nature 303:209 (1983); Bevan, Nucleic Acids Res. 12: 8711-8721 (1984); Klee et al., Bio-Technology 3(7): 637-642 (1985); and EPO publication 120,516. In addition to plant transformation vectors derived from the Ti or root-inducing (Ri) plasmids of Agrobacterium, alternative methods can be used to insert the DNA constructs of this invention into plant cells. Such methods may involve, but are not limited to, for example, the use of liposomes, electroporation, chemicals that increase free DNA uptake, free DNA delivery via microprojectile bombardment, and transformation using viruses or pollen.

A plasmid expression vector suitable for the introduction of a nucleic acid encoding a polypeptide or protein of the present invention in monocots using electroporation or particle-gun mediated transformation is composed of the following: a promoter that is constitutive or tissue-specific; an intron that provides a splice site to facilitate expression of the gene, such as the Hsp70 intron (PCT Publication WO93/19189); and a 3' polyadenylation sequence such as the nopaline synthase 3' sequence (NOS 3'; Fraley et al., Proc. Natl. Acad. Sci. USA 80: 4803-4807 (1983)). This expression cassette may be assembled on high copy replicons suitable for the production of large quantities of DNA.

An example of a useful Ti plasmid cassette vector for plant transformation is pMON17227. This vector is described in PCT Publication WO 92/04449 and contains a gene encoding an enzyme conferring glyphosate resistance (denominated CP4), which is an excellent selection marker gene for many plants. The gene is fused to the *Arabidopsis* EPSPS chloroplast transit peptide (CTP2) and expressed from the FMV promoter as described therein.

When adequate numbers of cells (or protoplasts) containing the exogenous nucleic acid encoding a polypeptide or protein of the present invention are obtained, the cells (or protoplasts) are regenerated into whole plants. Choice of methodology for the regeneration step is not critical, with suitable protocols being available for hosts from Leguminosae (alfalfa, soybean, clover, etc.), Umbelliferae (carrot, celery, parsnip), Cruciferae (cabbage, radish, canola/rapeseed, etc.), Cucurbitaceae (melons and cucumber), Gramineae (wheat, barley, rice, maize, etc.), Solanaceae (potato, tobacco, tomato, peppers), various floral crops, such as sunflower, and nut-bearing trees, such as almonds, cashews, walnuts, and pecans. See, for example, Ammirato et al., Handbook of Plant Cell Culture—Crop Species. Macmillan Publ. Co. (1984); Shimamoto et al., Nature 338:274-276 (1989); Fromm, UCLA Symposium on Molecular Strategies for Crop Improvement, Apr. 16-22, 1990. Keystone, Colo. (1990); Vasil et al., Bio/Technology 8:429-434 (1990); Vasil et al., Bio/Technology 10:667-674 (1992); Hayashimoto, Plant Physiol. 93:857-863 (1990); and Datta et al., Bio-technology 8:736-740 (1990). Regeneration can also be obtained from plant callus, explants, organs, or parts thereof. Such regeneration techniques are described generally in Klee et al., Ann. Rev. Plant Phys. 38:467-486 (1987).

A transgenic plant formed using *Agrobacterium* transformation methods typically contains a single exogenous gene on one chromosome. Such transgenic plants can be referred to as being heterozygous for the added exogenous gene. More preferred is a transgenic plant that is homozygous for the added exogenous gene; i.e., a transgenic plant that contains two added exogenous genes, one gene at the same locus on each chromosome of a chromosome pair. A homozygous transgenic plant can be obtained by sexually mating (selfing) an independent segregant transgenic plant that contains a single exogenous gene, germinating some of the seed produced and analyzing the resulting plants produced for the exogenous gene of interest.

The development or regeneration of transgenic plants containing the exogenous nucleic acid that encodes a polypeptide or protein of interest is well known in the art. Preferably, the regenerated plants are self-pollinated to provide homozygous transgenic plants, as discussed above. Otherwise, pollen obtained from the regenerated plants is crossed to seed-grown plants of agronomically important lines. Conversely, pollen from plants of these important lines is used to pollinate regenerated plants. A transgenic plant of the present invention containing a desired polypeptide or protein of the present invention is cultivated using methods well known to one skilled in the art.

Transgenic plants, that can be generated by practice of the present invention, include but are not limited to *Acacia*, alfalfa, aneth, apple, apricot, artichoke, arugula, asparagus, avocado, banana, barley, beans, beet, blackberry, blueberry, broccoli, brussels sprouts, cabbage, canola, cantaloupe, carrot, cassaya, cauliflower, celery, cherry, cilantro, citrus, clementines, coffee, corn, cotton, cucumber, Douglas fir, eggplant, endive, escarole, eucalyptus, fennel, figs, gourd, grape, grapefruit, honey dew, jicama, kiwifruit, lettuce, leeks, lemon, lime, Loblolly pine, mango, melon, mushroom, nut, oat, okra, onion, orange, an ornamental plant, papaya, parsley, pea, peach, peanut, pear, pepper, persimmon, pine, pineapple, plantain, plum, pomegranate, poplar, potato, pumpkin, quince, radiata pine, radicchio, radish, raspberry, rice, rye, sorghum, Southern pine, soybean, spinach, squash, strawberry, sugarbeet, sugarcane, sunflower, sweet potato, sweetgum, tangerine, tea, tobacco, tomato, turf, a vine, watermelon, wheat, yams, and zucchini.

The present invention also provides parts of the transgenic plants of present invention. Plant parts, without limitation, include seed, endospeiin, ovule and pollen. In a particularly preferred embodiment of the present invention, the plant part is a seed.

The present invention also further provides method for generating a transgenic plant comprising the steps of: a) introducing into the genome of the plant an exogenous nucleic acid, wherein the exogenous nucleic acid comprises in the 5' to 3' direction i) a promoter that functions in the cells of said plant, said promoter operably linked to; ii) a structural nucleic acid sequence encoding a polypeptide or protein of the present invention, said structural nucleic acid sequence operably linked to; iii) a 3' non-translated nucleic acid sequence that functions in said cells of said plant to cause transcriptional termination; b) obtaining transformed plant cells containing the nucleic acid sequence of step (a); and c) regenerating from said transformed plant cells a transformed plant in which said polypeptide or protein is overexpressed.

Any of the isolated nucleic acid molecules of the present invention may be introduced into a plant cell in a permanent or transient manner in combination with other genetic elements such as vectors, promoters, enhancers etc. Further any of the nucleic acid molecules encoding a *Xenorhabdus* protein or polypeptide of the present invention may be introduced into a plant cell in a manner that allows for over expression of the protein or polypeptide encoded by the nucleic acid molecule.

Antibodies have been expressed in plants (Hiatt et al., Nature 342:76-78 (1989); Conrad and Fielder, Plant Mol. Biol. 26:1023-1030 (1994)). Cytoplasmic expression of a scFv (single-chain Fv antibodies) has been reported to delay infection by artichoke mottled crinkle virus. Transgenic plants that express antibodies directed against endogenous proteins may exhibit a physiological effect (Philips et al., EMBO J. 16:4489-4496 (1997); Marion-Poll, Trends in Plant Science 2:447-448 (1997)). For example, expressed anti-abscisic antibodies reportedly result in a general perturbation of seed development (Philips et al., EMBO J. 16:4489-4496 (1997)).

Antibodies that are catalytic may also be expressed in plants (abzymes). The principle behind abzymes is that since antibodies may be raised against many molecules, this recognition ability can be directed toward generating antibodies that bind transition states to force a chemical reaction forward (Persidas, Nature Biotechnology 15:1313-1315 (1997); Baca et al., Ann. Rev. Biophys. Biomol. Struct. 26:461-493 (1997)). The catalytic abilities of abzymes may be enhanced by site directed mutagenesis. Examples of abzymes are, for example, set forth in U.S. Pat. Nos. 5,658,753; 5,632,990; 5,631,137; 5,602,015; 5,559,538; 5,576,174; 5,500,358; 5,318,897; 5,298,409; 5,258,289 and 5,194,585, all of which are herein incorporated in their entirety.

It is understood that any of the antibodies of the present invention may be expressed in plants and that such expression can result in a physiological effect. It is also understood that any of the expressed antibodies may be catalytic.

Microbial Constructs and Transformed Microbial Cells

The nucleotide sequences of the present invention may be introduced into a wide variety of prokaryotic and eukaryotic microorganism hosts to express the *Xenorhabdus* or *Photorhabdus* polypeptide or protein of interest, particularly the insect inhibitory polypeptides or proteins of the present invention. The term "microorganism" includes prokaryotic and eukaryotic microbial species such as bacteria and fungi. Fungi include yeast and filamentous fungi. Illustrative prokaryotes, both Gram-negative and Gram-positive, include Enterobacteriaceae, such as *Escherichia, Erwinia, Shigella, Salmonella,* and *Proteus*; Bacillaceae; Rhizobiceae, such as *Rhizobium*; Spirillaceae, such as *photobacterium, Zymomonas, Serratia, Aeromonas, Vibrio, Desulfovibrio, Spirillum*; Lactobacillaceae; Pseudomonadaceae, such as *Pseudomonas* and *Acetobacter*; Azotobacteraceae, Actinomycetales, and Nitrobacteraceae. Among eukaryotes are fungi, such as Phycomycetes and Ascomycetes, which includes yeast, such as *Saccharomyces* and *Schizosaccharomyces*; and Basidiomycetes yeast, such as *Rhodotorula, Aureobasidium, Sporobolomyces*, and the like.

For the purpose of plant protection against insects, a large number of microorganisms known to inhabit the phylloplane (the surface of the plant leaves) and/or the rhizosphere (the soil surrounding plant roots) of a wide variety of important crops may also be desirable host cells for manipulation, propagation, storage, delivery and/or mutagenesis of the disclosed recombinant constructs. These microorganisms include bacteria, algae, and fungi. Of particular interest are microorganisms, such as bacteria, e.g., genera *Bacillus* (including the species and subspecies *B. thuringiensis* kurstaki HD-1, *B. thuringiensis* kurstaki HD-73, *B. thuringiensis* sotto, *B. thuringiensis* berliner, *B. thuringiensis* thuringiensis, *B. thuringiensis* tolworthi, *B. thuringiensis* dendrolimus, *B. thuringiensis* alesti, *B. thuringiensis* galleriae, *B. thuringiensis* aizawai, *B. thuringiensis* subtoxicus, *B. thuringiensis* entomocidus, *B. thuringiensis* tenebrionis and *B. thuringiensis* san diego); *Pseudomonas, Erwinia, Serratia, Klebsiella, Zanthomonas, Streptomyces, Rhizobium, Rhodopseudomonas, Methylophilius, Agrobacterium, Acetobacter, Lactobacillus, Arthrobacter, Azotobacter, Leuconostoc*, and *Alcaligenes*; fungi, particularly yeast, e.g., genera *Saccharomyces, Cryptococcus, Kluyveromyces, Sporobolomyces, Rhodotorula*, and *Aureobasidium*. Of particular interest are such phytosphere bacterial species as *Pseudomonas syringae, Pseudomonas fluorescens, Serratia marcescens, Acetobacter xylinum, Agrobacterium tumefaciens, Rhodobacter sphaeroides, Xanthomonas campestris, Rhizobium melioti, Alcaligenes eutrophus*, and *Azotobacter vinlandii*; and phytosphere yeast species such as *Rhodotorula rubra, R. glutinis, R. marina, R. aurantiaca, Cryptococcus albidus, C. diffluens, C. laurentii, Saccharomyces rosei, S. pretoriensis, S. cerevisiae, Sporobolomyces roseus, S. odorus, Kluyveromyces veronae*, and *Aureobasidium pollulans*.

It is well known that exogenous nucleic acids encoding polypeptides of interest can be introduced into a microbial host cell, such as a bacterial cell or a fungal cell, using a recombinant construct. The present invention also relates to a fungal or bacterial recombinant construct comprising a structural nucleotide sequence encoding a *Xenorhabdus* or *Photorhabdus* protein or polypeptide. In a preferred embodiment, the structural nucleotide sequence encodes an insect inhibitory protein or polypeptide of the present invention. The present invention also relates to a bacterial or fungal cell comprising a bacterial or fungal recombinant vector. The present invention also relates to methods for obtaining a recombinant bacterial or fungal host cell, comprising introducing into a bacterial or fungal host cell an exogenous nucleic acid molecule.

The bacterial recombinant vector may be a linear or a closed circular plasmid. The vector system may be a single vector or plasmid or two or more vectors or plasmids which together contain the total DNA to be introduced into the genome of the bacterial host. In addition, the bacterial vector may be an expression vector. Nucleic acid molecules encoding *Xenorhabdus* proteins or polypeptide can, for example, be suitably inserted into a replicable vector for expression in a bacterium under the control of a suitable promoter for that bacterium. Many vectors are available for this purpose, and selection of the appropriate vector will depend mainly on the size of the nucleic acid to be inserted into the vector and the particular host cell to be transformed with the vector. Each vector contains various components depending on its function (amplification of DNA or expression of DNA) and the particular host cell with which it is compatible. The vector components for bacterial transformation generally include, but are not limited to, one or more of the following: a signal sequence, an origin of replication, one or more selectable marker genes, and an inducible promoter allowing the expression of exogenous DNA.

In general, plasmid vectors containing replicon and control sequences that are derived from species compatible with the host cell are used in connection with bacterial hosts. The vector ordinarily carries a replication site, as well as marking sequences that are capable of providing phenotypic selection in transformed cells. For example, *E. coli* is typically transformed using pBR322, a plasmid derived from an *E. coli* species (see, e.g., Bolivar et al., Gene 2:95 (1977)). pBR322 contains genes for ampicillin and tetracycline resistance and thus provides easy means for identifying transformed cells. The pBR322 plasmid, or other microbial plasmid or phage, also generally contains, or is modified to contain, promoters that can be used by the microbial organism for expression of the selectable marker genes.

Nucleic acid molecules encoding *Xenorhabdus* proteins or polypeptides may be expressed not only directly, but also as a fusion with another polypeptide, preferably a signal sequence or other polypeptide having a specific cleavage site at the N-terminus of the mature polypeptide. In general, the signal sequence may be a component of the vector, or it may be a part of the polypeptide encoding DNA that is inserted into the vector. The heterologous signal sequence selected should be one that is recognized and processed (i.e., cleaved by a signal peptidase) by the host cell. For bacterial host cells that do not recognize and process the native polypeptide signal sequence, the signal sequence is substituted by a bacterial signal sequence selected, for example, from the group consisting of the alkaline phosphatase, β-lactamase, or heat-stable enterotoxin II leaders and the like.

Both expression and cloning vectors contain a nucleotide sequence that enables the vector to replicate in one or more selected host cells. Generally, in cloning vectors this sequence is one that enables the vector to replicate independently of the host chromosomal DNA, and includes origins of replication or autonomously replicating sequences. Such sequences are well known for a variety of bacteria.

Expression and cloning vectors also generally contain a selection gene, also termed a selectable marker. This gene encodes a protein necessary for the survival or growth of transformed host cells grown in a selective culture medium. Host cells not transformed with the vector containing the selection gene will not survive in the culture medium. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for Bacilli. One example of a selection scheme utilizes a drug to arrest growth of a host cell. Those cells that are successfully transformed with a heterologous protein homologue or fragment thereof produce a protein conferring drug resistance and thus survive the selection regimen.

The expression vector for producing a polypeptide can also contains an inducible promoter that is recognized by the host bacterial organism and is operably linked to the nucleic acid encoding, for example, the nucleic acid molecule encoding the *Xenorhabdus* protein or polypeptide of interest. Inducible promoters suitable for use with bacterial hosts include the β-lactamase, *E. coli* λ phage PL and PR, and *E. coli* galactose, arabinose, alkaline phosphatase, tryptophan (trp), and lactose operon promoter systems and variations thereof (Chang et al., Nature 275:615 (1978); Goeddel et al., Nature 281:544 (1979); Guzman et al., J. Bacteriol. 174:7716-7728 (1992); Goeddel, Nucleic Acids Res. 8:4057 (1980); EP 36,776) and hybrid promoters such as the tac promoter (deBoer et al., Proc. Natl. Acad. Sci. (USA) 80:21-25 (1983)). However, other known bacterial inducible promoters are suitable (Siebenlist et al., Cel120:269 (1980)).

Promoters for use in bacterial systems also generally contain a Shine-Dalgarno (S.D.) sequence or a consensus sequence thereof operably linked to the DNA encoding the polypeptide of interest. The promoter can be removed from the bacterial source DNA by restriction enzyme digestion and inserted into the vector containing the desired DNA coding sequence, or vice versa.

Alternatively, the expression constructs can be integrated into the bacterial genome with an integrating vector. Integrating vectors typically contain at least one sequence homologous to the bacterial chromosome that allows the vector to integrate. Integrations appear to result from recombinations between homologous DNA in the vector and the bacterial chromosome. For example, integrating vectors constructed with DNA from various *Bacillus* strains integrate into the *Bacillus* chromosome (E.P.O. Pub. No. 127,328). Integrating vectors may also be comprised of bacteriophage or transposon sequences.

Construction of suitable vectors containing one or more of the above-listed components employs standard recombinant DNA techniques. Isolated plasmids or DNA fragments are cleaved, tailored, and re-ligated in the form desired to generate the plasmids required. Examples of available bacterial expression vectors include, but are not limited to, the multifunctional *E. coli* cloning and expression vectors such as Bluescript™ (Stratagene, La Jolla, Calif.), in which, for example, a *xenorhabdus* protein or polypeptide of the present invention, may be ligated into the vector in frame with sequences for the amino-terminal Met and the subsequent 7 residues of β-galactosidase so that a hybrid protein is produced; pIN vectors (Van Heeke and Schuster J. Biol. Chem. 264:5503-5509 (1989)); and the like. pGEX vectors (Promega, Madison Wis.) may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems are designed to include heparin, thrombin or factor XA protease cleavage sites so that the cloned polypeptide of interest can be released from the GST moiety at will.

It is, of course, necessary to select the appropriate bacteria taking into consideration replicability of the replicon in the cells of a bacterium. For example, *E. coli, Serratia*, or *Salmonella* species can be suitably used as the host when well known plasmids such as pBR322, pBR325, pACYC177, or pKN410 are used to supply the replicon. *E. coli* strain W3110 is a preferred host or parent host because it is a common host strain for recombinant DNA product fermentations. Preferably, the host cell should secrete minimal amounts of proteolytic enzymes.

Host cells are transfected and preferably transformed with the above-described vectors and cultured in conventional nutrient media modified as appropriate for inducing promoters, selecting transformants, or amplifying the genes encoding the desired sequences.

Numerous methods of transfection are known to the ordinarily skilled artisan, for example, calcium phosphate and electroporation. Depending on the host cell used, transformation is done using standard techniques appropriate to such cells. The calcium treatment employing calcium chloride, as described in section 1.82 of Sambrook et al., Molecular Cloning: A Laboratory Manual, New York: Cold Spring Harbor Laboratory Press, (1989), is generally used for bacterial cells that contain substantial cell-wall barriers. Another method for transformation employs polyethylene glycol/DMSO, as described in Chung and Miller (Chung and Miller, Nucleic Acids Res. 16:3580 (1988)). Yet another method is the use of the technique termed electroporation. In addition, bacterial cells can be readily transformed using various forms of phages (i.e., transducing, temperate, lytic and lysogenic), suicide vectors for inserting DNA directly into the chromosome, and through homologous recombination using either phages, suicide vectors or linear DNA.

Bacterial cells used to produce the polypeptide of interest for purposes of this invention are cultured in suitable media in which the promoters for the nucleic acid encoding the heterologous polypeptide can be artificially induced as described generally, e.g., in Sambrook et al., Molecular Cloning: A Laboratory Manual, New York: Cold Spring Harbor Laboratory Press, (1989). Examples of suitable media are given in U.S. Pat. Nos. 5,304,472 and 5,342,763.

A yeast recombinant construct can typically include one or more of the following: a promoter sequence, fusion partner sequence, leader sequence, transcription termination sequence, a selectable marker. These elements can be combined into an expression cassette, which may be maintained in a replicon, such as an extrachromosomal element (e.g., plasmids) capable of stable maintenance in a host, such as yeast or bacteria. The replicon may have two replication systems, thus allowing it to be maintained, for example, in yeast for expression and in a procaryotic host for cloning and amplification. Examples of such yeast-bacteria shuttle vectors include YEp24 (Botstein et al., Gene, 8:17-24 (1979)), pCl/1 (Brake et al., Proc. Natl. Acad. Sci. USA, 81:4642-4646 (1984)), and YRp17 (Stinchcomb et al., J. Mol. Biol., 158:157 (1982)). In addition, a replicon may be either a high or low copy number plasmid. A high copy number plasmid will generally have a copy number ranging from about 5 to about 200, and typically about 10 to about 150. A host containing a high copy number plasmid will preferably have at least about 10, and more preferably at least about 20.

Useful yeast promoter sequences can be derived from genes encoding enzymes in the metabolic pathway. Examples of such genes include alcohol dehydrogenase (ADH) (E.P.O. Pub. No. 284044), enolase, glucokinase, glucose-6-phosphate isomerase, glyceraldehyde-3-phosphate-dehydrogenase (GAP or GAPDH), hexokinase, phosphofructokinase, 3-phosphoglycerate mutase, and pyruvate kinase (PyK) (E.P.O. Pub. No. 329203). The yeast PHO5 gene, encoding acid phosphatase, also provides useful promoter sequences (Myanohara et al., Proc. Natl. Acad. Sci. USA, 80:1 (1983)). In addition, synthetic promoters which do not occur in nature also function as yeast promoters. Examples of such hybrid promoters include the ADH regulatory sequence linked to the GAP transcription activation region (U.S. Pat. Nos. 4,876, 197 and 4,880,734). Other examples of hybrid promoters include promoters which consist of the regulatory sequences of either the ADH2, GAL4, GAL10, or PHO5 genes, combined with the transcriptional activation region of a glycolytic enzyme gene such as GAP or PyK (E.P.O. Pub. No. 164556). Furthermore, a yeast promoter can include naturally occurring promoters of non-yeast origin that have the ability to bind yeast RNA polymerase and initiate transcription. Examples of such promoters include, inter alia, (Cohen et al., Proc. Natl. Acad. Sci. USA, 77:1078 (1980); Henikoff et al., Nature 283:835 (1981); Hollenberg et al., Curr. Topics Microbiol. Immunol., 96:119 (1981); Mercereau-Puigalon et al., Gene, 11:163 (1980); and Panthier et al., Curr. Genet., 2:109 (1980)).

Intracellularly expressed fusion proteins provide an alternative to direct expression of the polypeptides of interest. Typically, a DNA sequence encoding the N-terminal portion of a stable protein, a fusion partner, is fused to the 5' end of heterologous structural nucleotide sequence encoding the desired polypeptide. Upon expression, this construct will provide a fusion of the two amino acid sequences. The DNA sequence at the junction of the two amino acid sequences may or may not encode a cleavable site. See, e.g., E.P.O. Pub. No. 196056. Another example is a ubiquitin fusion protein. Such a ubiquitin fusion protein preferably retains a site for a processing enzyme (e.g. ubiquitin-specific processing protease) to cleave the ubiquitin from the polypeptide of the present invention. Through this method, therefore, a mature polypeptide can be isolated [see, P.C.T. WO 88/024066].

Alternatively, polypeptides or proteins can also be secreted from the cell into the growth media by creating chimeric DNA molecules that encode a fusion protein comprised of a leader sequence fragment that provides for secretion in yeast of the polypeptides. Preferably, there are processing sites encoded between the leader fragment and the polypeptide-encoding sequence fragment that can be cleaved either in vivo or in vitro. The leader sequence fragment typically encodes a signal peptide comprised of hydrophobic amino acids which direct the secretion of the protein from the cell.

DNA encoding suitable signal sequences can be derived from genes for secreted yeast proteins, such as the yeast invertase gene (E.P.O. Pub. No. 12873; J.P.O. Pub. No. 62,096,086) and the A-factor gene (U.S. Pat. No. 4,588,684). Alternatively, leaders of non-yeast origin, such as an interferon leader, exist that also provide for secretion in yeast (E.P.O. Pub. No. 60057).

A preferred class of secretion leaders are those that employ a fragment of the yeast alpha-factor gene, which contains both a "pre" signal sequence, and a "pro" region. The types of alpha-factor fragments that can be employed include the full-length pre-pro alpha factor leader (about 83 amino acid residues) as well as truncated alpha-factor leaders (typically about 25 to about 50 amino acid residues) (U.S. Pat. Nos. 4,546,083 and 4,870,008; and E.P.O. Pub. No. 324274). Additional leaders employing an alpha-factor leader fragment that provides for secretion include hybrid alpha-factor leaders made with a pre-sequence of a first yeast, but a pro-region from a second yeast alpha factor. See, e.g., P.C.T. WO 89/02463.

Examples of transcription terminator sequence and other yeast-recognized termination sequences, such as those coding for glycolytic enzymes, are known to those of skill in the art.

Alternatively, the expression constructs can be integrated into the yeast genome with an integrating vector. Integrating vectors typically contain at least one sequence homologous to a yeast chromosome that allows the vector to integrate, and preferably contain two homologous sequences flanking the expression construct. Integrations appear to result from recombinations between homologous DNA in the vector and the yeast chromosome (Orr-Weaver et al., Methods in Enzymol., 101:228-245 (1983)). An integrating vector may be directed to a specific locus in yeast by selecting the appropriate homologous sequence for inclusion in the vector. See On-Weaver et al., supra. One or more expression constructs may integrate, possibly affecting levels of recombinant protein produced (Rine et al., Proc. Natl. Acad. Sci. USA, 80:6750 (1983)). The chromosomal sequences included in the vector can occur either as a single segment in the vector, which results in the integration of the entire vector, or as two segments homologous to adjacent segments in the chromosome and flanking the expression construct in the vector, which results in the stable integration of only the expression construct.

Expression and transformation vectors, either extrachromosomal replicons or integrating vectors, have been developed for transformation into many yeasts. For example, expression vectors have been developed for, inter alia, the following yeasts: *Candida albicans* (Kurtz, et al., Mol. Cell. Biol., 6:142 (1986)), *Candida maltosa* (Kunze et al., J. Basic Microbiol., 25:141 (1985)); *Hansenula polymorpha* (Gleeson et al., J. Gen. Microbiol. 132:3459 (1986); Roggenkamp et al., Mol. Gen. Genet. 202:302 (1986)); *Kluyveromyces fragilis* (Das et al., J. Bacteriol. 158:1165 (1984)); *Kluyveromyces lactis* (De Louvencourt et al., J. Bacteriol. 154:737 (1983); Van den Berg et al., Bio/Technology 8:135 (1990)); *Pichia guillerimondii* (Kunze et al., J. Basic Microbiol. 25:141 (1985)); *Pichia pastoris* (Cregg et al., Mol. Cell. Biol. 5:3376 (1985); U.S. Pat. Nos. 4,837,148 and 4,929,555); *Saccharomyces cerevisiae* (Hinnen et al., Proc. Natl. Acad. Sci. USA 75:1929 (1978); Ito et al., J. Bacteriol. 153:163 (1983)); *Schizosaccharomyces pombe* (Beach and Nurse, Nature 300:706 (1981)); and *Yarrowia lipolytica* (Davidow, et al., Curr. Genet. 10:380471 (1985); and Gaillardin et al., Curr. Genet. 10:49 (1985)).

Methods of introducing exogenous nucleic acids into yeast hosts are well-known in the art, and typically include either the transformation of spheroplasts or of intact yeast cells treated with alkali cations. Transformation procedures usually vary with the yeast species to be transformed. See e.g., Kurtz et al., Mol. Cell. Biol. 6:142 (1986); Kunze et al., J. Basic Microbiol. 25:141 (1985) for *Candida*. See, e.g., Gleeson et al., J. Gen. Microbiol. 132:3459 (1986); Roggenkamp et al., Mol. Gen. Genet. 202:302 (1986) for *Hansenula*. See, e.g., Das et al., J. Bacteriol. 158:1165 (1984); De Louvencourt et al., J. Bacteriol. 154:1165 (1983); Van den Berg et al., Bio/Technology 8:135 (1990) for *Kluyveromyces*. See, e.g., Cregg et al., Mol. Cell. Biol. 5:3376 (1985); Kunze et al., J. Basic Microbiol. 25:141 (1985); U.S. Pat. Nos. 4,837,148 and 4,929,555 for *Pichia*. See, e.g., Hinnen et al., Proc. Natl. Acad. Sci. USA 75:1929 (1978); Ito et al., J. Bacteriol. 153: 163 (1983) for *Saccharomyces*. See, e.g., Beach and Nurse, Nature 300:706 (1981) for *Schizosaccharomyces*. See, e.g., Davidow et al., Curr. Genet. 10:39 (1985); Gaillardin et al., Curr. Genet. 10:49 (1985) for *Yarrowia*.

In order to obtain expression polypeptides or proteins of interest, recombinant microbial host cells derived from the transformants are incubated under conditions which allow expression of the recombinant polypeptide-encoding sequence. These conditions will vary, dependent upon the host cell selected. However, the conditions are readily ascertainable to those of ordinary skill and knowledge in the art.

Detection of polypeptides expressed in the transformed host cell may be performed by several methods. For example, a polypeptide or protein may be detected by its immunological reactivity with antibodies.

Polypeptides or proteins of the present invention may be isolated from the cell by lysis, if formed intracellularly, or isolated from the culture medium, if secreted, by conventional methods.

Computer Media

The nucleotide sequence provided in SEQ ID NO:1 or fragment thereof, or complement thereof, or a nucleotide sequence at least 90% identical, preferably 95% or 98% identical, even more preferably 99% or 100% identical to the sequence provided in SEQ ID NO:1 or fragment thereof, or complement thereof, can be "provided" in a variety of mediums to facilitate use. Such a medium can also provide a subset thereof in a form that allows a skilled artisan to examine the sequences.

In one application of this embodiment, a nucleotide sequence of the present invention can be recorded on computer readable media. As used herein, "computer readable media" refers to any medium that can be read and accessed directly by a computer. Such media include, but are not limited to: magnetic storage media, such as floppy discs, hard disc, storage medium, and magnetic tape: optical storage media such as CD-ROM; electrical storage media such as RAM and ROM; and hybrids of these categories such as magnetic/optical storage media. A skilled artisan can readily appreciate how any of the presently known computer readable mediums can be used to create a manufacture comprising computer readable medium having recorded thereon a nucleotide sequence of the present invention.

As used herein, "recorded" refers to a process for storing information on computer readable medium. A skilled artisan can readily adopt any of the presently known methods for recording information on computer readable medium to generate media comprising the nucleotide sequence information of the present invention. A variety of data storage structures are available to a skilled artisan for creating a computer readable medium having recorded thereon a nucleotide sequence of the present invention. The choice of the data storage structure will generally be based on the means chosen to access the stored information. In addition, a variety of data processor programs and formats can be used to store the nucleotide sequence information of the present invention on computer readable medium. The sequence information can be represented in a word processing text file, formatted in commercially-available software such as WordPerfect and Microsoft Word, or represented in the form of an ASCII file, stored in a database application, such as DB2, Sybase, Oracle, or the like. A skilled artisan can readily adapt any number of data processor structuring formats (e.g. text file or database) in order to obtain computer readable medium having recorded thereon the nucleotide sequence information of the present invention.

By providing one or more of nucleotide sequences of the present invention, a skilled artisan can routinely access the sequence information for a variety of purposes. Computer software is publicly available which allows a skilled artisan to access sequence information provided in a computer readable medium. The examples which follow demonstrate how software which implements the BLAST (Altschul et al., J. Mol. Biol. 215:403-410 (1990)) and BLAZE (Brutlag et al., Comp. Chem. 17:203-207 (1993)) search algorithms on a Sybase system can be used to identify open reading frames (ORFs) within the genome that contain homology to ORFs or proteins from other organisms. Such ORFs are protein-encoding fragments within the sequences of the present invention and are useful in producing commercially important proteins such as enzymes used in amino acid biosynthesis, metabolism, transcription, translation, RNA processing, nucleic acid and a protein degradation, protein modification, and DNA replication, restriction, modification, recombination, and repair.

The present invention further provides systems, particularly computer-based systems, which contain the sequence information described herein. Such systems are designed to identify commercially important fragments of the nucleic acid molecule of the present invention. As used herein, "a computer-based system" refers to the hardware means, software means, and data storage means used to analyze the nucleotide sequence information of the present invention. The minimum hardware means of the computer-based systems of the present invention comprises a central processing unit (CPU), input means, output means, and data storage means. A skilled artisan can readily appreciate that any one of the currently available computer-based system are suitable for use in the present invention.

As indicated above, the computer-based systems of the present invention comprise a data storage means having stored therein a nucleotide sequence of the present invention and the necessary hardware means and software means for supporting and implementing a search means. As used herein, "data storage means" refers to memory that can store nucleotide sequence information of the present invention, or a memory access means which can access manufactures having recorded thereon the nucleotide sequence information of the present invention. As used herein, "search means" refers to one or more programs which are implemented on the computer-based system to compare a target sequence or target structural motif with the sequence information stored within the data storage means. Search means are used to identify fragments or regions of the sequence of the present invention that match a particular target sequence or target motif A variety of known algorithms are disclosed publicly and a variety of commercially available software for conducting search means are available can be used in the computer-based systems of the present invention. Examples of such software include, but are not limited to, MacPattern (EMBL), BLASTIN and BLASTIX (NCBIA). One of the available algorithms or implementing software packages for conducting homology searches can be adapted for use in the present computer-based systems.

The most preferred sequence length of a target sequence is from about 10 to 100 amino acids or from about 30 to 300 nucleotide residues. However, it is well recognized that during searches for commercially important fragments of the nucleic acid molecules of the present invention, such as sequence fragments involved in gene expression and protein processing, may be of shorter length.

As used herein, "a target structural motif," or "target motif," refers to any rationally selected sequence or combination of sequences in which the sequences the sequence(s) are chosen based on a three-dimensional configuration which is formed upon the folding of the target motif. There are a variety of target motifs known in the art. Protein target motifs include, but are not limited to, enzymatic active sites and signal sequences. Nucleic acid target motifs include, but are not limited to, promoter sequences, cis elements, hairpin structures and inducible expression elements (protein binding sequences).

Thus, the present invention further provides an input means for receiving a target sequence, a data storage means for storing the target sequences of the present invention sequence identified using a search means as described above, and an output means for outputting the identified homologous sequences. A variety of structural formats for the input and output means can be used to input and output information in the computer-based systems of the present invention. A preferred format for an output means ranks fragments of the sequence of the present invention by varying degrees of homology to the target sequence or target motif. Such presentation provides a skilled artisan with a ranking of sequences which contain various amounts of the target sequence or target motif and identifies the degree of homology contained in the identified fragment.

A variety of comparing means can be used to compare a target sequence or target motif with the data storage means to identify sequence fragments sequence of the present invention. For example, implementing software which implement the BLAST and BLAZE algorithms (Altschul et al., J. Mol. Biol. 215:403-410 (1990)) can be used to identify open frames within the nucleic acid molecules of the present invention. A skilled artisan can readily recognize that any one of the publicly available homology search programs can be used as the search means for the computer-based systems of the present invention.

Exemplary Uses of the Agents of the Present Invention

Nucleic acid molecules and fragments thereof of the present invention may be employed to obtain other nucleic acid molecules from the same or closely related species. Such nucleic acid molecules include the nucleic acid molecules that encode the complete coding sequence of a protein and promoters and flanking sequences of such molecules. In addition, such nucleic acid molecules include nucleic acid molecules that encode for other isozymes or gene family members. Such molecules can be readily obtained by using the above-described nucleic acid molecules or fragments thereof to screen genomic libraries obtained from *Xenorhabdus*. Methods for forming such libraries are well known in the art.

Nucleic acid molecules and fragments thereof of the present invention may also be employed to obtain other nucleic acid molecules such as nucleic acid homologues. Such homologues include the nucleic acid homologues of non-*Xenorhabdus* species including the nucleic acid molecules that encode, in whole or in part, protein homologues of other species or other organisms, sequences of genetic elements such as promoters and transcriptional regulatory elements. Such molecules can be readily obtained by using the above-described nucleic acid molecules or fragments thereof to screen cDNA or genomic libraries. Methods for forming such libraries are well known in the art. Such homologue molecules may differ in their nucleotide sequences from those found in one or more of the nucleotide sequences disclosed in US Patent Application Publication No. 20110167520 A1, which is incorporated herein by reference in its entirety, or complements thereof because complete complementarity is not needed for stable hybridization. The nucleic acid molecules of the present invention therefore also include molecules that, although capable of specifically hybridizing with the nucleic acid molecules may lack "complete complementarity." In a particular embodiment, methods or 3' or 5' RACE may be used (Frohman, M. A. et al., Proc. Natl. Acad. Sci. (U.S.A.) 85:8998-9002 (1988); Ohara, O. et al., Proc. Natl. Acad. Sci. (U.S.A.) 86:5673-5677 (1989)) to obtain such sequences.

Any of a variety of methods may be used to obtain one or more of the above-described nucleic acid molecules (Zamechik et al., Proc. Natl. Acad. Sci. (U.S.A.) 83:4143-4146 (1986); Goodchild et al., Proc. Natl. Acad. Sci. (U.S.A.) 85: 5507-5511 (1988); Wickstrom et al., Proc. Natl. Acad. Sci. (U.S.A.) 85:1028-1032 (1988); Holt et al., Molec. Cell. Biol. 8:963-973 (1988); Gerwirtz et al., Science 242: 1303-1306 (1988); Anfossi et al., Proc. Natl. Acad. Sci. (U.S.A.) 86:3379-3383 (1989); Becker et al., EMBO J. 8:3685-3691 (1989)). Automated nucleic acid synthesizers may be employed for this purpose. In lieu of such synthesis, the disclosed nucleic acid molecules may be used to define a pair of primers that can be used with the polymerase chain reaction (Mullis et al., Cold Spring Harbor Symp. Quant. Biol. 51:263-273 (1986); Erlich et al., European Patent 50,424; European Patent 84,796, European Patent 258,017; European Patent 237,362; Mullis, European Patent 201,184; Mullis et al., U.S. Pat. No. 4,683,202; Erlich, U.S. Pat. No. 4,582,788; and Saiki et al., U.S. Pat. No. 4,683,194) to amplify and obtain any desired nucleic acid molecule or fragment.

The nucleic acid molecules of the present invention may be used for physical mapping. Physical mapping, in conjunction with linkage analysis, can enable the isolation of genes. Physical mapping has been reported to identify the markers closest in terms of genetic recombination to a gene target for cloning. Once a DNA marker is linked to a gene of interest, the chromosome walking technique can be used to find the genes via overlapping clones. For chromosome walking, random molecular markers or established molecular linkage maps are used to conduct a search to localize the gene adjacent to one or more markers. A chromosome walk (Bukanov and Berg, Mo. Microbiol. 11:509-523 (1994); Birkenbihl and Vielmetter Nucleic Acids Res. 17:5057-5069 (1989); Wenzel and Herrmann, Nucleic Acids Res. 16:8323-8336 (1988) is then initiated from the closest linked marker. Starting from the selected clones, labeled probes specific for the ends of the insert DNA are synthesized and used as probes in hybridizations against a representative library. Clones hybridizing with one of the probes are picked and serve as templates for the synthesis of new probes; by subsequent analysis, contigs are produced.

The degree of overlap of the hybridizing clones used to produce a contig can be determined by comparative restriction analysis. Comparative restriction analysis can be carried out in different ways all of which exploit the same principle; two clones of a library are very likely to overlap if they contain a limited number of restriction sites for one or more restriction endonucleases located at the same distance from each other. The most frequently used procedures are, fingerprinting (Coulson et al, Proc. Natl. Acad. Sci. (U.S.A.) 83:7821-7821, (1986); Knott et al., Nucleic Acids Res. 16:2601-2612 (1988); Eiglmeier et al., Mol. Microbiol. 7:197-206 (1993), 1993), restriction fragment mapping (Smith and Birnstiel, Nucleic Acids Res. 3:2387-2398 (1976)); or the "landmarking" technique (Charlebois et al. J. Mol. Biol. 222:509-524 (1991)).

It is understood that the nucleic acid molecules of the present invention may in one embodiment be used in physical mapping. In a preferred embodiment, nucleic acid molecules of the present invention may in one embodiment be used in the physical mapping of *Xenorhabdus*.

Nucleic acid molecules of the present invention can be used in comparative mapping. Comparative mapping within families provides a method to assess the degree of sequence conservation, gene order, ploidy of species, ancestral relationships and the rates at which individual genomes are evolving. Comparative mapping has been carried out by cross-hybridizing molecular markers across species within a given family. As in genetic mapping, molecular markers are needed but instead of direct hybridization to mapping filters, the markers are used to select large insert clones from a total genomic DNA library of a related species. The selected clones, each a representative of a single marker, can then be used to physically map the region in the target species. The advantage of this method for comparative mapping is that no mapping population or linkage map of the target species is needed and the clones may also be used in other closely related species. By comparing the results obtained by genetic mapping in model organisms, with those from other species, similarities of genomic structure among species can be established. Cross-hybridization of RFLP markers has been reported and conserved gene order has been established in many studies. Such macroscopic synteny is utilized for the estimation of correspondence of loci among these organisms. It is understood that markers of the present invention may in another embodiment be used in comparative mapping. In a preferred embodiment the markers of present invention may be used in the comparative mapping of spore-forming Gram-positive bacteria.

In an aspect of the present invention, one or more of the agents of the present invention may be used to detecting the presence, absence or level of an organism, preferably a *Xenorhabdus* in a sample. In another aspect of the present invention, one or more of the nucleic molecules of the present invention are used to determine the level (i.e., the concentration of mRNA in a sample, etc.) or pattern (i.e., the kinetics of expression, rate of decomposition, stability profile, etc.) of the expression encoded in part or whole by one or more of the nucleic acid molecule of the present invention (collectively, the "Expression Response" of a cell or tissue). As used herein, the Expression Response manifested by a cell or tissue is said to be "altered" if it differs from the Expression Response of cells or tissues of organisms not exhibiting the phenotype. To determine whether a Expression Response is altered, the Expression Response manifested by the cell or tissue of the organism exhibiting the phenotype is compared with that of a similar cell or tissue sample of a organism not exhibiting the phenotype. As will be appreciated, it is not necessary to re-determine the Expression Response of the cell or tissue sample of organisms not exhibiting the phenotype each time such a comparison is made; rather, the Expression Response of a particular organism may be compared with previously obtained values of normal organism. As used herein, the phenotype of the organism is any of one or more characteristics of an organism.

Nucleic acid molecules of the present invention can be used to monitor expression. A microarray-based method for high-throughput monitoring of gene expression may be utilized to measure gene-specific hybridization targets. This 'chip'-based approach involves using microarrays of nucleic acid molecules as gene-specific hybridization targets to quantitatively measure expression of the corresponding genes (Schena et al., Science 270:467-470 (1995); Shalon, Ph.D. Thesis, Stanford University (1996)). Every nucleotide in a large sequence can be queried at the same time. Hybridization can be used to efficiently analyze nucleotide sequences.

Several microarray methods have been described. One method compares the sequences to be analyzed by hybridization to a set of oligonucleotides or cDNA molecules representing all possible subsequences (Bains and Smith, J. Theor. Biol. 135:303 (1989)). A second method hybridizes the sample to an array of oligonucleotide or cDNA probes. An array consisting of oligonucleotides or cDNA molecules complementary to subsequences of a target sequence can be used to determine the identity of a target sequence, measure its amount, and detect differences between the target and a reference sequence. Nucleic acid molecules microarrays may also be screened with protein molecules or fragments thereof to determine nucleic acid molecules that specifically bind protein molecules or fragments thereof.

The microarray approach may also be used with polypeptide targets (U.S. Pat. No. 5,445,934; U.S. Pat. No. 5,143,854; U.S. Pat. No. 5,079,600; U.S. Pat. No. 4,923,901). Essentially, polypeptides are synthesized on a substrate (microarray) and these polypeptides can be screened with either protein molecules or fragments thereof or nucleic acid molecules in order to screen for either protein molecules or fragments thereof or nucleic acid molecules that specifically bind the target polypeptides (Fodor et al., Science 251:767-773 (1991)).

It is understood that one or more of the molecules of the present invention, preferably one or more of the nucleic acid molecules or protein molecules or fragments thereof of the present invention may be utilized in a microarray based method. In a preferred embodiment of the present invention, one or more of the *Xenorhabdus* nucleic acid molecules or protein or polypeptide molecules or fragments thereof of the present invention may be utilized in a microarray based method. A particular preferred microarray embodiment of the present invention is a microarray comprising nucleic acid molecules encoding genes or fragments thereof that are homologues of known genes or nucleic acid molecules that comprise genes or fragments thereof that elicit only limited or no matches to known genes. A further preferred microarray embodiment of the present invention is a microarray comprising nucleic acid molecules having genes or fragments thereof that are homologues of known genes and nucleic acid molecules that comprise genes or fragment thereof that elicit only limited or no matches to known genes.

In a preferred embodiment, the microarray of the present invention comprises at least 10 nucleic acid molecules that specifically hybridize under stringent conditions to at least 10 nucleic acid molecules encoding *Xenorhabdus* proteins or polypeptides or fragments thereof set forth in the tables of US Patent Application Publication No. 20110167520 A1, which is incorporated herein by reference in its entirety. In a more preferred embodiment, the microarray of the present invention comprises at least 100 nucleic acid molecules that specifically hybridize under stringent conditions to at least 100 nucleic acid molecules that encode a *Xenorhabdus* protein or polypeptide or fragment thereof set forth therein. In an even more preferred embodiment, the microarray of the present invention comprises at least 1,000 nucleic acid molecules that specifically hybridize under stringent conditions to at least 1,000 nucleic acid molecules that encode a *Xenorhabdus* protein or polypeptide or fragment thereof set forth therein. In a further even more preferred embodiment, the microarray of the present invention comprises at least 2,500 nucleic acid molecules that specifically hybridize under stringent conditions to at least 2,500 nucleic acid molecules that encode a

*Xenorhabdus* protein or polypeptide or fragment thereof set forth therein. While it is understood that a single nucleic acid molecule may encode more than one protein homologue or fragment thereof, in a preferred embodiment, at least 50%, preferably at least 70%, more preferably at least 80%, even more preferably at least 90% of the nucleic acid molecules that comprise the microarray contain one protein or fragment thereof.

In a preferred embodiment, the microarray of the present invention comprises at least 10 nucleic acid molecules that specifically hybridize under stringent conditions to at least 10 nucleic acid molecules selected from the nucleotide sequences disclosed in the aforementioned US Patent Application Publication No. 20110167520 A1, or fragment thereof or complement of either. In a more preferred embodiment, the microarray of the present invention comprises at least 100 nucleic acid molecules that specifically hybridize under stringent conditions to at least 100 nucleic acid molecules that encode a *Xenorhabdus* protein or polypeptide or fragment thereof set forth in the tables of the aforementioned US Patent Application Publication No. 20110167520 A1. In an even more preferred embodiment, the microarray of the present invention comprises at least 1,000 nucleic acid molecules that specifically hybridize under stringent conditions to at least 1,000 nucleic acid molecules that encode a *Xenorhabdus* protein or polypeptide or fragment thereof set forth therein. In a further even more preferred embodiment, the microarray of the present invention comprises at least 2,500 nucleic acid molecules that specifically hybridize under stringent conditions to at least 2,500 nucleic acid molecules that encode a *Xenorhabdus* protein or fragment thereof set forth therein. While it is understood that a single nucleic acid molecule may encode more than one protein homologue or fragment thereof, in a preferred embodiment, at least 50%, preferably at least 70%, more preferably at least 80%, even more preferably at least 90% of the nucleic acid molecules that comprise the microarray contain one protein homologue or fragment thereof.

Nucleic acid molecules of the present invention may be used in site directed mutagenesis. Site-directed mutagenesis may be utilized to modify nucleic acid sequences, particularly as it is a technique that allows one or more of the amino acids encoded by a nucleic acid molecule to be altered (e.g. a threonine to be replaced by a methionine). Three basic methods for site-directed mutagenesis are often employed. These are cassette mutagenesis (Wells et al., Gene 34:315-23 (1985)); primer extension (Gilliam et al., Gene 12:129-137 (1980)); Zoller and Smith, Methods Enzymol. 100:468-500 (1983); and Dalbadie-McFarland et al., Proc. Natl. Acad. Sci. (U.S.A.) 79:6409-6413 (1982)) and methods based upon PCR (Scharf et al., Science 233:1076-1078 (1986); Higuchi et al., Nucleic Acids Res. 16:7351-7367 (1988)). Site-directed mutagenesis approaches are also described in European Patent 0 385 962, European Patent 0 359 472, and PCT Patent Application WO 93/07278.

Site-directed mutagenesis strategies have been applied to plants for both in vitro as well as in vivo site-directed mutagenesis (Lanz et al., J. Biol. Chem. 266:9971-9976 (1991); Kovgan and Zhdanov, Biotekhnologiya 5: 148-154, No. 207160n, Chemical Abstracts 110: 225 (1989); Ge et al., Proc. Natl. Acad. Sci. (U.S.A.) 86:4037-4041 (1989), Zhu et al., J. Biol. Chem. 271:18494-18498 (1996), Chu et al., Biochemistry 33:6150-6157 (1994), Small et al., EMBO J. 11:1291-1296 (1992), Cho et al., Mol. Biotechnol. 8:13-16 (1997), Kita et al., J. Biol. Chem. 271:26529-26535 (1996), Jin et al., Mol. Microbiol. 7:555-562 (1993), Hatfield and Vierstra, J. Biol. Chem. 267:14799-14803 (1992), Zhao et al., Biochemistry 31:5093-5099 (1992)).

Any of the nucleic acid molecules of the present invention may either be modified by site-directed mutagenesis or used as, for example, nucleic acid molecules that are used to target other nucleic acid molecules for modification. It is understood that mutants with more than one altered nucleotide can be constructed using techniques that practitioners skilled in the art are familiar with such as isolating restriction fragments and ligating such fragments into an expression vector (see, for example, Sambrook et al., Molecular Cloning: A Laboratory Manual, Cold Spring Harbor Press (1989)). In a preferred embodiment of the present invention, one or more of the nucleic acid molecules or fragments thereof of the present invention may be modified by site-directed mutagenesis.

In addition to the above discussed procedures, practitioners are familiar with the standard resource materials which describe specific conditions and procedures for the construction, manipulation and isolation of macromolecules (e.g., DNA molecules, plasmids, etc.), generation of recombinant organisms and the screening and isolating of clones, (see for example, Sambrook et al., Molecular Cloning: A Laboratory Manual, Cold Spring Harbor Press (1989); Mailga et al., Methods in Plant Molecular Biology, Cold Spring Harbor Press (1995); Birren et al., Genome Analysis: Analyzing DNA, 1, Cold Spring Harbor, N.Y.).

Insect inhibitory protein-encoding nucleic acids of the present invention will find particular uses in the plant protection against insects. For instance, insect-resistant transgenic plants can be generated by introducing the exogenous nucleic acids encoding an insect inhibitory polypeptide or protein or insect inhibitory fragment thereof, the amino acid sequence of which is substantially identical to SEQ ID NO:2. Another example is to engineer transgenic microorganism (bacteria or fungi) to express insect inhibitory polypeptides or proteins of the present invention and then to apply them to the insect food source or allow them to reside in soil surrounding plant roots or on the surface of plant leaves.

The transgenic microorganisms of the present invention may be used to produce *Xenorhabdus* or *Photorhabdus* polypeptides or proteins of interest, particularly insect inhibitory polypeptides or proteins. Insect inhibitory polypeptides or proteins or insect inhibitory fragments thereof may be secreted, for example as in bacterial systems, meaning targeted to either the periplasm as for gram negative bacteria or localized to the extracellular space for gram negative or any other type of bacterium, or localized to the intracellular spaces within the cytoplasm. Such compositions may be administered to insects according to methods well known in the art. For example, insect inhibitory polypeptides or proteins of the present invention may be formulated as sprayable compositions or as a bait matrix.

The principle object of the present invention is to provide a method for identification of any gene or any protein encoded by any structural gene contained within a *Xenorhabdus* or *Photorhabdus* species, particularly those species which are shown to exhibit the production of an insect inhibitory protein or molecule or other similarly active composition, either alone or in combination with proteins or molecules or other similarly active compositions which may be derived from the bacterium in its role as natural symbiont within an insect pathogenic nematode host.

The present invention provides first for the isolation and identification of one or more nematodes which have the capacity for invading an insect larvae or adult, typically an insect of any order including but not limited to Coleopteran, Dipteran, Hemipteran, Lepidopteran, Homopteran, Hymenopteran, or *Lygus*, white fly, or any sucking or piercing insect species. The isolation and identification of a single insect pathogenic nematode species then enables the skilled artisan to isolate at least one species of *Xenorhabdus* or *Photorhabdus* endosymbiotic bacteria from the haemolymphe of an insect larvae or adult which has been invaded by the isolated and identified host nematode.

Nematodes can be isolated using methods particularly taught herein and in view of the prior art. Typically, one or more larvae of the genus and species *Galleria melonella* is/are placed into a soil sample under proper humidity and temperature conditions for a period of time to allow the larvae to be invaded and colonized by a nematode species. It is generally believed from observations of nematode invasions that once a single nematode species invades a single larvae or adult insect and successfully releases bacterial symbionts of either *Xenorhabdus* or *Photorhabdus* bacteria (which is further dependent upon the species of host nematode successfully invading the insect body), then an effective colonization of the insect haemolymphe by the bacterium so released results in colonization of that particular insect host body to that genus and species of nematode and bacterium. This may be analogous to bacteriophage restriction inhibition, a phenomenon well known in the bacterial art, and may be a means for ensuring that the bacterium and nematode host-symbiont relationship is maintained.

The symbiont bacterium released into the haemolymphe then produces fungicides, acaricides, and antibacterial compounds which assist in this restriction of growth to the category and class or genus and species of nematode and bacterium affiliated with the host-symbiont relationship. It may be that the nematode plays some functional role in this relationship, providing one or more specific factors, compositions, or accessory proteins, small molecules or compositions which enable the released symbiont bacterium to sense the genus and species of the host insect body, possibly in association with factors, proteins, or accessory compositions or receptors present within the haemolymphe of the pathogenized insect which enable the bacterium to switch on or express proteins which are effective in limiting the insect hosts' defenses, if any, which would otherwise lead to an ineffective invasion and infection by the nematode and bacterium. Particularly relevant to this possibility is the presence as disclosed herein of several insect inhibitory proteins identified by their predicted structure, size and relationship to previously identified *Photorhabdus* insect inhibitory proteins from protein families such as Tcc, Tca, Tcb and Tcd (Ensign et al., WO 97/17432; and Ensign et al., WO 98/08932) encoded by an equal number of similar but substantially different genes. Interestingly, the invasion of different insect genus/species hosts by a single insect pathogenic nematode which releases a single *Xenorhabdus* bacterium species into the haemolymphe enables the skilled artisan to isolate the bacterium from each of the individual insect host bodies. Presumably, one skilled in classical microbiological methodologies would expect that the same bacterium now isolated and purified from each of the different cadavers onto selective media, followed by the growth and analysis of each isolate in an identical broth medium for identical periods of time and under identical conditions, would otherwise result in a similar protein profile when analyzing the spent medium from such an experiment. However, the inventors herein have identified the surprising result that the protein profile of each isolate isolated and purified from different cadaver species produce drastically different extracellular protein profiles when examined by 2D gel analysis. This result suggests the possibility that the host insect, or the nematode, or the combination of the two, or alternatively merely the bacterium functions to sense its environment and switches some genes on and others off to express proteins and compositions which function in some particular yet unidentified manner specific for its host environment. The difference in protein profiles of bacterium isolated from different cadaver species, yet presumably released as a single species from a single nematode host may be the result of at least a rearrangement the genome of the bacterium either by transposition or inversion or a combination of the two means to produce an otherwise isogenic line of bacterium capable of expressing an insect host selective combination of proteins which enable the nematode-bacterium host-symbiont relationship to maximize its chances for survival. This result may also suggest that the nematode, although playing host to a bacterium which is capable of expressing a variety of proteins which individually are capable of inhibiting or killing specific insect host species, may preferably invade a selective genus or species of insect for which it is more aptly suited in its particular host-symbiont relationship.

Nevertheless, the isolation and purification of an insect pathogenic nematode *Xenorhabdus* or *Photorhabdus* symbiont bacterium from an insect cadaver provides the basis for obtaining an amount of genomic DNA from which a genomic library can be constructed to represent the entire genome of the bacterial strain. The library can then be manipulated as described herein to produce linear nucleotide sequences, which can then be compared to each other to identify regions of identity with which an overlapping sequence can be generated to produce islands of linear sequence known as contigs because of the contiguous linear sequence assembled from smaller bits of sequence data. The contigs can be assembled into a genomic map from which genes can be identified, and wherein translation of structural genes lead to further identification of proteins having predicted structure and function based on homologies of such predicted protein sequences as translated from open reading frames contained within the genome map, to proteins of known sequence, and perhaps also of known structure and function identified previously from other bacterial, viral, fungal, or other eukaryotic sources.

Syringomycins are bioactive lipodepsipeptides originally isolated from the phytopathogenic bacterium *Pseudomonas syringae* pv. *Syringae*. These compounds are potent fungicides which inhibit the growth of *Saccharomyces cerevisiae* and *Aspergilus niger* by forming pores in the plasma membrane. In addition, polypeptides generated from these proteins have also been shown to have fungicidal activity. The *Xenorhabdus* genomic DNA sequences disclosed herein contains at least 11 open reading frames encoding predicted proteins displaying homology to syringomycin. These open reading frames range in size from 4000-11, 500 base pairs and are exemplified by sequences shown in the tables in the US Patent Application Publication No. 20110167520 A1, which is incorporated herein by reference in its entirety. Any of these predicted proteins or polypeptides derived from these proteins have potential antimicrobial activity with commercial applications.

Insecticidal Compositions

The inventors contemplate that the *Xenorhabdus* strain and isolatable protein compositions exhibiting insecticidal activity as disclosed herein will find particular utility as insecticides for topical and/or systemic application to field crops, grasses, fruits and vegetables, and ornamental plants. In a preferred embodiment, the bioinsecticide composition comprises an oil flowable suspension of bacterial cells which expresses a novel crystal protein disclosed herein. Preferably the cells are *Xenorhabdus* Xs85816 cells, however, any such bacterial host cell expressing the novel nucleic acid segments disclosed herein and producing an insecticidal protein is contemplated to be useful, such as *B. thuringiensis, B. megaterium, B. subtilis, E. coli, Salmonella typhimurium*, other *Xenorhabdus* or *Photorhabdus* species, or *Pseudomonas* spp.

In another important embodiment, the bioinsecticide composition comprises a water dispersible granule. This granule comprises bacterial cells which expresses a novel insecticidal protein disclosed herein. Preferred bacterial cells are *Xenorhabdus* Xs85816 cells, however, bacteria such as *B. thuringiensis, B. megaterium, B. subtilis, E. coli, Salmonella typhimurium*, other *Xenorhabdus* or *Photorhabdus* species, or *Pseudomonas* spp. cells transformed with a DNA segment disclosed herein and expressing the insecticidal protein are also contemplated to be useful.

In a third important embodiment, the bioinsecticide composition comprises a wettable powder, dust, pellet, or collodial concentrate. This powder comprises bacterial cells which expresses a novel insecticidal protein disclosed herein. Preferred bacterial cells are *Xenorhabdus* Xs85816 cells, however, bacteria such as *B. thuringiensis, B. megaterium, B. subtilis, E. coli, Salmonella typhimurium*, other *Xenorhabdus* or *Photorhabdus* species, or *Pseudomonas* spp. cells transformed with a DNA segment disclosed herein and expressing the insecticidal protein are also contemplated to be useful. Such dry forms of the insecticidal compositions may be formulated to dissolve immediately upon wetting, or alternatively, dissolve in a controlled-release, sustained-release, or other time-dependent manner.

In a fourth important embodiment, the bioinsecticide composition comprises an aqueous suspension of bacterial cells such as those described above which express the insecticidal protein. Such aqueous suspensions may be provided as a concentrated stock solution which is diluted prior to application, or alternatively, as a diluted solution ready-to-apply.

For these methods involving application of bacterial cells, the cellular host containing the insecticidal protein gene(s) may be grown in any convenient nutrient medium, where the DNA construct provides a selective advantage, providing for a selective medium so that substantially all or all of the cells retain the *Xenorhabdus* gene. These cells may then be harvested in accordance with conventional ways. Alternatively, the cells can be treated prior to harvesting.

When the insecticidal compositions comprise intact *Xenorhabdus* cells expressing the protein of interest, such bacteria may be formulated in a variety of ways. They may be employed as wettable powders, granules or dusts, by mixing with various inert materials, such as inorganic minerals (phyllosilicates, carbonates, sulfates, phosphates, and the like) or botanical materials (powdered corncobs, rice hulls, walnut shells, and the like). The formulations may include spreader-sticker adjuvants, stabilizing agents, other pesticidal additives, or surfactants. Liquid formulations may be aqueous-based or non-aqueous and employed as foams, suspensions, emulsifiable concentrates, or the like. The ingredients may include rheological agents, surfactants, emulsifiers, dispersants, or polymers.

Alternatively, the novel Xip insecticidal proteins may be prepared by native or recombinant bacterial expression systems in vitro and isolated for subsequent field application. Such protein may be either in crude cell lysates, suspensions, colloids, etc., or alternatively may be purified, refined, buffered, and/or further processed, before formulating in an active biocidal formulation. Likewise, under certain circumstances, it may be desirable to isolate insecticidal proteins or whole cells from bacterial cultures expressing the insecticidal Xip protein(s) and apply solutions, suspensions, or collodial preparations of such insecticidal proteins or whole cells as the active bioinsecticidal composition.

Regardless of the method of application, the amount of the active component(s) is applied at an insecticidally-effective amount, which will vary depending on such factors as, for example, the specific coleopteran insects to be controlled, or the specific piercing and sucking insect to be controlled, the specific plant or crop to be treated, the environmental conditions, and the method, rate, and quantity of application of the insecticidally-active composition.

The insecticide compositions described may be made by formulating either the bacterial cell, insecticidal protein suspension, or isolated protein component with the desired agriculturally-acceptable carrier. The compositions may be formulated prior to administration in an appropriate means such as lyophilized, freeze-dried, dessicated, or in an aqueous carrier, medium or suitable diluent, such as saline or other buffer. The formulated compositions may be in the form of a dust or granular material, or a suspension in oil (vegetable or mineral), or water or oil/water emulsions, or as a wettable powder, or in combination with any other carrier material suitable for agricultural application. Suitable agricultural carriers can be solid or liquid and are well known in the art. The term "agriculturally-acceptable carrier" covers all adjuvants, e.g., inert components, dispersants, surfactants, tackifiers, binders, etc. that are ordinarily used in insecticide formulation technology; these are well known to those skilled in insecticide formulation. The formulations may be mixed with one or more solid or liquid adjuvants and prepared by various means, e.g., by homogeneously mixing, blending and/or grinding the insecticidal composition with suitable adjuvants using conventional formulation techniques.

The insecticidal compositions of this invention are applied to the environment of the target coleopteran or piercing and sucking insect, typically onto the foliage of the plant or crop to be protected, by conventional methods, preferably by spraying. The strength and duration of insecticidal application will be set with regard to conditions specific to the particular pest(s), crop(s) to be treated and particular environmental conditions. The proportional ratio of active ingredient to carrier will naturally depend on the chemical nature, solubility, and stability of the insecticidal composition, as well as the particular formulation contemplated.

Other application techniques, e.g., dusting, sprinkling, soaking, soil injection, seed coating, seedling coating, spraying, aerating, misting, atomizing, and the like, are also feasible and may be required under certain circumstances such as e.g., insects that cause root or stalk infestation, or for application to delicate vegetation or ornamental plants. These application procedures are also well-known to those of skill in the art.

The insecticidal composition of the invention may be employed in the method of the invention singly or in combination with other compounds, including and not limited to other pesticides. The method of the invention may also be used in conjunction with other treatments such as surfactants, detergents, polymers or time-release formulations. The insecticidal compositions of the present invention may be formulated for either systemic or topical use.

The concentration of insecticidal composition which is used for environmental, systemic, or foliar application will vary widely depending upon the nature of the particular formulation, means of application, environmental conditions, and degree of biocidal activity. Typically, the bioinsecticidal composition will be present in the applied formulation at a concentration of at least about 1% by weight and may be up to and including about 99% by weight. Dry formulations of the compositions may be from about 1% to about 99% or more by weight of the composition, while liquid formulations may generally comprise from about 1% to about 99% or more of the active ingredient by weight. Formulations which comprise intact bacterial cells will generally contain from about 104 to about 107 cells/mg.

The insecticidal formulation may be administered to a particular plant or target area in one or more applications as needed, with a typical field application rate per hectare ranging on the order of from about 50 g to about 500 g of active ingredient, or of from about 500 g to about 1000 g, or of from about 1000 g to about 5000 g or more of active ingredient.

Having now generally described the invention, the same will be more readily understood through reference to the following examples which are provided by way of illustration, and are not intended to be limiting of the present invention, unless specified.

EXAMPLE 1

Isolation of Entomopathogenic Nematodes

Entomopathogenic nematodes were isolated from soil samples obtained from various geographic locations according to the following procedure. Generally the practice in the art is to infest soil samples with larvae of the insect species *Galleria mellonella*. This example describes an entomopathogenic nematode baiting method not practiced in the art which does not utilize *Galleria mellonella*, a non-pest and therefore a non-target insect species in baiting nematodes. Instead, this method describes isolation of entomopathogenic nematodes having a greater insect inhibitory diversity by baiting with pest species and therefore target insect larvae. This method selects for nematode and *Xenorhabdus* and *Photorhabdus* bacterial strains having a greater diversity in their insect inhibitory properties and a greater diversity and variety of insect inhibitory proteins active against specific target insects.

Approximately 4 liters of soil sample by volume was placed into a plastic ziplock bag. The soil sample was then infested with a variety of 4th instar target insects, e.g. corn ear worm, tobacco bud worm, black cut worm, beet army worm, boll weevil, corn root worm, as well as the non-target insect larvae *Galleria mellonella*. The insect larvae infested soil bags were zip sealed and incubated at 25° C. in the dark for about 72 hours. Dead insect larvae were removed from the soil samples and identified as to genus and species, washed in a mild NaOH/NaClO solution (50 ml water, 2 ml 4M NaOH, 1 ml 5% conc. NaClO), rinsed with sterile water and placed into modified nematode traps (White, Science 66:302-303 (1927)). The modified trap consists of the following elements assembled in order from bottom to top: (1) the bottom of a 4 inch diameter petri dish half filled with water, (2) the lid of a 2 inch petri dish floating in the water, (3) a dead insect larvae potentially infested with entomopathogenic nematodes placed onto a layer of Whatman filter paper laying on the bottom of the inside of the smaller petri dish; (4) covered with the lid of the 4 inch diameter petri dish. This modified "White Trap" is incubated at 25° C. in the dark and left undisturbed for 7-14 days. Infective juvenile stages of the nematodes begin to emerge from the insect cadaver after one to two weeks and enter the water surrounding the smaller diameter petri dish, forming a suspension containing the nematodes. The nematode infested suspension is collected, placed into tissue culture flasks and these remain viable for several months when stored at 12-16° C. in the dark.

As an example of the efficacy of this method, a *Steinernema kraussei* nematode strain (#68) was previously isolated from a soil sample into which was placed only live *Galleria mellonella* larvae. A dead *G. mellonella* larvae was subsequently harvested and the sole nematode species isolated from the larvae was strain #68 (Mracek and Wester, J. Nematol. 25:710-717; 1993). Strain #68 was assayed for its insect inhibitory effects on larvae of the agricultural target insect pests corn earworm, black cutworm and beet armyworm as well as *Galleria mellonella*. Six 4th instar larvae for each species were placed individually into wells of a 24 well microtiter dish, each well being bottom lined with a disc of Whatman filter paper. Ten microliters of a strain #68 nematode suspension, obtained and maintained as described above, was placed into each well and incubated in the dark at 25° C. for three days. Larvae were then analyzed for survival, morbidity, and mortality. Unexpectedly, *G. mellonella* was not affected by nematode infestation, however all of the agricultural pest species were infected and killed. The agricultural pest larvae were surface sterilized and their haemolymphe was streaked onto NBTA indicator agar plates. Single *Xenorhabdus* colonies were isolated and sub-cultured to eliminate the presence of any possible contaminating bacteria and ensure pure *Xenorhabdus* cultures. The *Xenorhabdus* bacteria isolated from corn earworm, black cutworm and beet armyworm were then grown for 48 hours in liquid BHI medium. In order to access both extracellular and cell bound components which may be insect inhibitory, the culture was first subjected to a freeze thaw cycle, and then centrifuged and filtered (0.2 μm), and the resulting lysate was separated from insoluble material. The lysate was maintained at −70° C. unless used immediately. A 2D gel analysis of the filtrate was completed to determine the protein profiles of each supernatant in triplicate. Surprisingly, bacterial protein profiles of bacteria harvested from corn earworm larvae were similar to each other, but very different from the protein profiles of bacteria isolated from either black cutworm or beet armyworm insect larvae. This result suggests that a single strain of *Xenorhabdus* bacteria may be conditioned to express insect genus specific inhibitory proteins.

EXAMPLE 2

Isolation of Symbiotic Bacteria

Symbiotic bacteria were isolated from entomopathogenic nematodes according to the following procedure. A variety of 4th instar insect larvae (corn ear worm, tobacco bud worm, black cut worm, beet army worm, boll weevil, corn root worm, and also *Galleria mellonella*) was placed in a 24 well plate containing Whatman filters in each well. Approx. 10 μl of entomopathogenic nematodes suspension was added into each well containing one insect. The 24 well plates were sealed with parafilm and placed at 25° C. in the dark.

After 48 to 72 hours dead insect larvae were removed from the 24-well plate. The insect larvae were surface sterilized (20 ml water, 3 ml 4M NaOH and 1 ml 5% NaOCl) for 5 minutes and air-dried. The insect larvae were cut open with sterile instruments on the lateral side without injuring the gut and the haemolymphe was streaked on indicator agar (nutrient bromothymol blue agar and nutrient agar). The agar plates were incubated at 30° C. in the dark for 48 hours.

Characteristic colonies were selected from the indicator plates: phase I *Xenorhabdus* bacteria are able to take up bromothymol blue dye from the nutrient agar and form blue colonies. Bacterial characterization was performed according to methods known to the one skilled in the art (Farmer (1984), Bergey's Manual of Systematic Bacteriology, Vol. 1: 510-511; Akhurst & Boemare (1988), J. Gen. Microbiol., Vol. 133: 1835-1845; Boemare et al. (1993), Int. J. Syst. Bacteriol., Vol. 44: 249-255).

Single characteristic phase I colonies were picked up by an inoculation loop and suspended into BHI media (Brain Heart Infusion medium (Difco), 32 g/l, 50 ml in a 250 ml baffled flask). The bacteria were grown at 25° C. at 280 rpm on a rotary shaker in the dark. After 24 hours 15% glycerol was added to the bacterial culture, 1.5 ml aliquots for stock cultures were placed into cryovials and stored at −80° C.

EXAMPLE 3

Genomic Library Construction

*Xenorhabdus* strain Xs85816 was isolated and purified according to methods described in examples 1 and 2 herein. Strain Xs85816 was associated with substantial insecticidal activity directed to *lygus* and boll weevil. Strain Xs85816 was deposited according to the Budapets Treaty on the International Recognition of the Deposit of Microorganisms for the Purpose of Patent Procedures with the Agriculture Research Culture Collection (NRRL) International Depositary Authority at 1815 North University Street, in Peoria, Ill. ZIP 61604 U.S.A. on Jun. 22, 2000 and designated as NRRLB-30306, after having first been shown to exhibit insecticidal activity against piercing and sucking insects, in particular against *lygus* species, and against boll weevil, and is contemplated as a source for DNA sequences encoding insecticidal proteins, and when formulated into a composition of matter as a spray, powder or emulsion, for the treatment of plants or animals to inhibit insect infestation. Xs85816 bacterial cells were grown in brain heart infusion broth (Difco) for 42 hours at 25° C. to mid-exponential phase (OD650=~1.0). Cells were poured into 10 1.5 ml-microfuge tubes and spun for 5 minutes at ~10,000 RPM to pellet. The supernatant was removed and the cells were frozen. The frozen pellets were resuspended into 200 μl of TE (10 mM Tris 1 mM EDTA pH 8.0). Genomic DNA was prepared from the frozen cell pellets using the Promega Genomic Preparation kit following the instructions of the manufacturer. Ten DNA samples were prepared from the cells above, and two of the samples were resuspended into 50 μl of TE. Sample purity was tested and confirmed by digestion using the restriction enzymes EcoRI, HindIII, NotI, and SalI. The resuspended samples were used for the preparation of a genomic library.

The genomic library of *Xenorhabdus* strain Xs85816 was prepared according to standard procedures well known to those skilled in the art. Sheared DNA was polished with T4 polymerase and T4 polynucleotide kinase. Fragments 2-3 kb in length were recovered from an agarose gel. BstXI linkers were then attached to the ends of the recovered fragments. BstXI linkers consisted of two oligos capable of hybridizing to each other over a portion of the length of one of the oligos, and providing a 3' four base overhang consisting of 5'-CACA-3'. Linker-ligated 2-3 kb fragments were gel purified and ligated into the BstXI digested plasmid vector pJCP2 and transformed into *E. coli* DH10B. BstXI cuts twice within pJCP2, inactivating/removing a neomycin phosphotransferase coding sequence and leaving identical 3' overhangs consisting of 5'-TGTG-3'. The resulting vector fragment contains an intact beta-lactamase coding sequence enabling selection of transformed cells containing genomic insertions into the exposed BstXI overhangs on media containing ampicillin Several ampicillin resistant transformants were selected and streaked in duplicate onto media containing either ampicillin or kanamycin to determine the efficiency of the library construction. Greater than 95% of colonies arising from the transformation contained an insert, presumably derived from the genomic sequences. However, the insertion frequency was probably somewhat lower because of the opportunity for the BstXI excised nptII coding sequence to re-insert in an inverted orientation or BstXI adapter itself to be ligated and inserted into plasmid. Approximately 200,000 colony forming units per microliter of ligation mix were obtained. About thirty thousand individual recombinant colonies were selected for DNA sequence analysis of inserted genomic DNA.

EXAMPLE 4

Generation and Assembly of *Xenorhabdus* sp. Genome Sequence

This example serves to illustrate the generation of the 1017 contigs and singletons listed in the Sequence Listing. About 58000 genomic nucleotide sequence traces were derived from the double stranded plasmid library as described in Example 3. The two basic methods for the DNA sequencing are the chain termination method of Sanger et al., Proc. Natl. Acad. Sci. (U.S.A.) 74:5463-5467 (1977) and the chemical degradation method of Maxam and Gilbert, Proc. Natl. Acad. Sci. (U.S.A.) 74:560-564 (1977) using automated fluorescence-based sequencing as reported by Craxton, Method, 2:20-26 (1991); Ju et al., Proc. Natl. Acad. Sci. (U.S.A.) 92:4347-4351 (1995); and Tabor and Richardson, Proc. Natl. Acad. Sci. (U.S.A.) 92:6339-6343 (1995) and high speed capillary gel electrophoresis, e.g. as disclosed by Swerdlow and Gesteland, Nucleic Acids Res. 18:1415-1419 (1990); Smith, Nature 349:812-813 (1991); Luckey et al., Methods Enzymol. 218:154-172 (1993); Lu et al., J. Chromatog. A. 680: 497-501 (1994); Carson et al., Anal. Chem. 65:3219-3226 (1993); Huang et al., Anal. Chem. 64:2149-2154 (1992); Kheterpal et al., Electrophoresis 17:1852-1859 (1996); Quesada and Zhang, Electrophoresis 17:1841-1851 (1996);

Baba, Yakugaku Zasshi 117:265-281 (1997). For instance, genomic nucleotide sequence traces are generated using a 377 or 3700 DNA Sequencer (Perkin-Elmer Corp., Applied Biosystems Div., Foster City, Calif.) allowing for rapid electrophoresis and data collection. With these types of automated systems, fluorescent dye-labeled sequence reaction products are detected and chromatograms are subsequently viewed, stored in a computer and analyzed using corresponding apparatus-related software programs. These methods are known to those of skill in the art and have been described and reviewed (Birren et al., Genome Analysis: Analyzing DNA, 1, Cold Spring Harbor, N.Y.

PHRED (phragment editor), which is developed by Phil Green at the University of Washington, was used to call the bases from the sequence trace files and to assign quality scores to the bases. PHRED uses Fourier methods to examine the four base traces in the region surrounding each point in the data set in order to predict a series of evenly spaced predicted locations. That is, it determines where the peaks would be centered if there were no compressions, dropouts, or other factors shifting the peaks from their "true" locations. Next, PHRED examines each trace to find the centers of the actual, or observed peaks and the areas of these peaks relative to their neighbors. The peaks are detected independently along each of the four traces so many peaks overlap. A dynamic programming algorithm is used to match the observed peaks detected in the second step with the predicted peak locations found in the first step. Default parameters were used in the base calling.

After the base calling is completed, sequence preprocessing is performed by removing 5' and 3' vector and linker sequences, according to standard procedures well known in the art.

The preprocessed sequences were then assembled into contigs, or groups of overlapping sequences. Contigs are assembled using PHRAP (phragment assembly program) developed by Phil Green at the University of Washington (http://www.mbt.washington.edu) using default assembly parameters. This program takes a file of shotgun sequences and compiles consensus contig sequences. Alignments are influenced by quality scores, based on Green's algorithm. Singletons are the remaining sequences without sufficient overlaps with others after the assembly. The contigs and singletons files and their corresponding quality files were united to create "islands".

A total of 1017 contigs and singletons were obtained. Contig sequences are recognized as those sequences whose designations begin with XEN10C. Singleton sequences are recognized as those having designations which begin with gC-xewcLIB371. All contig and singleton sequences were run through the annotation and gene selection processes as described in Example 5.

EXAMPLE 5

Identification of *Xenorhabdus* sp. Genes

This example illustrates the identification of genes within the 1017 contig and singleton sequences assembled as described in Example 4. The genes and partial genes embedded in such contigs and singletons were identified through a series of informatic analyses. Homology-based searches (i.e., BLASTX) were used to detect conserved sequences during comparisons of DNA sequences or hypothetically translated protein sequences to public and/or proprietary DNA and protein databases. Existence of an *Xenorhabdus* sp. gene was inferred if significant sequence similarity extended over the majority of the target gene. Novel genes, i.e., with no known homologs, were predicted with the program GeneMark, which calculates the probability of a gene based on the presence of a gene-like 'grammar' in the DNA sequence (i.e., start and stop signals, and a significant open reading frame) and statistical analyses of protein-coding potential through biases in putative codon usage. The results of the homology and predictive methods were then merged into a single set of predicted coding regions, and their most probable translation.

The homology-based method used to define the *Xenorhabdus* sp. gene set was BLASTX. For a description of BLASTX see Coulson, Trends in Biotechnology 12:76-80 (1994) and Birren et al., Genome Analysis, 1:543-559 (1997). BLASTX takes a nucleotide sequence, translates it in three forward reading frames and three reverse complement reading frames, and then compares the six translations against a protein sequence database (e.g. the non-redundant protein (i.e., nr-aa) database maintained by the National Center for Biotechnology Information as part of GenBank and available at the web site: http://www.ncbi.nlm.nih.gov). BLASTX is run with the *Xenorhabdus* sp. contigs and singletons as queries against the GenBank non-redundant protein data library identified as "nr-aa". To identify genes solely by BLASTX, the maximum BLASTX E value is set at 1E-08.

The ab initio method used to define the *Xenorhabdus* sp. gene set was GeneMark. (see http://genemark.biology.gatech.edu/GeneMark for details). GeneMark uses inhomogeneous Markov chain models derived from comparisons of known coding and non-coding sequences to predict the presence of protein-coding regions.

In Table 1 below (modified from Table 1 of the US Patent Application Publication No. 20110167520 A1, which is incorporated herein by reference in its entirety), GroEL protein encoding regions in the *Xenorhabdus* nucleic acid molecules of the present invention are identified and results of the BLAST and GeneMark analyses provided. Where the predicted protein has a match to a homolog in the non-redundant protein database, the confidence in accuracy of the gene prediction is proportional to the Bit score. "Bits" refers to information content, and the score in the "Bits" column indicates the amount of information in the hit. A higher bit score indicates a better match. Low complexity matches (which can generate high BLAST scores if they match over long stretches with other low quality data) are inherently low information content, and hence do not generate high "bit scores". Where the protein has been predicted by GeneMark, the confidence in accuracy of the gene prediction is proportional to the GeneMark probability score. The higher the probability score, the more likely the DNA sequence is transcribed into mRNA and translated into protein. Many, but not all, proteins are predicted by both BLASTX and by GeneMark. In these instances, both Bit scores and GeneMark probabilities are provided.

TABLE 1

Xenorhabdus Xs85816 Nucleic Acid Sequences, Encoded Proteins, & Annotations

| SEQ ID No. | Contig/ Singleton ID | Position: Start-Stop | Polypepetide SEQ ID No. | NCBI gi | Bitscore | E value | %_ident | %_cvrg | Prob. (GM) | NCBI gi Description |
|---|---|---|---|---|---|---|---|---|---|---|
| 1 | XEN10C258 | 653-1537 | 2 | g6225121 | 476 | 1.00E-159 | 89 | 51 | 0.87 | 60 KD CHAPERONIN (PROTEIN CPN60) (GROEL PROTEIN) [*Enterobacter amnigenus*] |

SEQ ID No.: Provides the SEQ ID NO listed in the Sequence Listing for the contig or singleton in which the protein encoding region is identified.
Contig/Singleton ID: Provides the identification assigned to the contig or singleton in which the protein encoding region is identified.
Position: Start-Stop: Indicates location of the identified protein encoding region within the contig or singleton. In cases where the first numeral is higher than its corresponding second numeral, the *Xenorhabdus* sp. protein or fragment thereof is encoded by the complement of the sequence set forth in the sequence listing.
Polypeptide SEQ ID NO: The sequence identification number of the amino acid sequence of the polypeptide encoded by the identified open reading frame in the contig or singleton.
NCBI gi: Refers to National Center for Biotechnology Information GenBank Identifier number which is the best match for a given contig or singleton region from which the protein encoding region was identified.
Bit Score: Bit score for BLAST match
E value: The expected number of distinct segment pairs between two sequences with a score above the bit score.
%_ident: Refers to the percentage of identically matched nucleotides (or residues) that exist along the length of that portion of the sequences which is aligned by the BLAST comparison.
%_cvrg: Refers to the percent of hit sequence length that matches to the query sequence in the match generated using BLAST (% cvrg = (match length/hit total length) × 100).
Prob. (GM): A measure of the likelihood that a region of DNA codes for a protein sequence as determined by the gene-predicting program GeneMark.
NCBI gi Description: A description of the database entry referenced in the "NCBI gi" column. Sequences were analyzed by BLASTX against the non-redundant protein database maintained by NCBI, and a description of the top hit is provided.

The translation for each predicted protein into strings of amino acids is provided. These predicted translations are the most probable, given the initiation and termination codons, and the biases in codon usage seen in publicly available *Xenorhabdus* genes.

Coding sequences identified in Table 1 of the aforementioned US Patent Application Publication No. 20110167520 A1, encode many useful *Xenorhabdus* polypeptides or proteins, including but not limited to insect inhibitory polypeptides or proteins, polypeptides or proteins capable of conferring antibiotic resistance, cytotoxin proteins which may be used as microbial inhibitory proteins including bactericidal, bacteriostatic, fungicidal, and fungistatic polypeptides or proteins, polyketide synthases, polypeptides or proteins capable of conferring resistance to heavy metals or other toxic compositions, transposons and mobile genetic elements and their corresponding transposases, excisases, integrases, and invertases, phage and phage particle proteins, transcription regulatory proteins, translation regulatory proteins, and other useful proteins homologous to proteins derived from *Xenorhabdus, Photorhabdus, Serratia, Yersinia, Salmonella, E. coli*, and *Erwinia* sp. Specifically, the coding sequence as set forth in SEQ ID NO:1 encodes a GroEL protein.

EXAMPLE 6

Functional utility of insect inhibitory proteins produced by *Xenorhabdus* (or *Photorhabdus*) was tested using the following or a similar procedure. 50 ml BHI medium in a 250 ml baffled flask was inoculated with 1.5 ml bacterial stock culture and grown at 25° C. and 280 rpm on a rotary shaker in the dark. After 48 hours the culture was frozen at −80° C. for at least 24 hours. The culture broth was then thawed, centrifuged at 2600×g for 30 minutes at 4° C. and decanted from the cell and debris pellet. The broth was then sterile-filtered (0.2 µm) and dialyzed. The culture supernatant was used without an additional concentration step for bioassays to evaluate insect inhibitory, fungicidal and bactericidal properties. Larvae were obtained using insect eggs obtained from commercial sources, hatched and reared using conventional insectary methods.

Insect inhibitory activity was observed against western corn rootworm (WCR) and cotton boll weevil which are members of the insect order Coleoptera. The WCR is a member of the family Chrysomelidae. Other members of the Chrysomelid family include the Colorado potato beetle, the flea and leaf beetles. The cotton boll weevil is a member of the family Curculionidae which includes stored grains pests such as the rice and maize weevils and billbugs. Other Coleoptera include wireworms, seed-feeding bruchids, and grubs.

Insect inhibitory activity against western corn rootworm larvae was tested as follows. *Xenorhabdus* culture supernatant, control medium (BHI) or Tris buffer, pH 7.0, was applied to the surface (about 0.38 cm2) of a modified artificial diet (Bioserv™; diet product F9757) in 20 µl aliquots. The plates were allowed to air-dry in a drying chamber (16-20° C.; 40-50% RH) and the wells were infested with single non-diapausing neonate western corn rootworm (Coleoptera: *Diabrotica virgifera virgifera* LeConte) hatched from surface disinfested eggs (Pleau, M., 1999. Master of Science Thesis., Nutritional physiology of *Diabrotica virgifera*. Saint Louis University). Plates were sealed, placed in a humidified growth chamber and maintained at 27° C. for the appropriate period (5-7 days). Mortality and stunting (0-3) scores were then assessed and statistically analyzed (SAS institute, 1989-1997. User's manual for JMP version 3.2). Generally, 24 insects per treatment were used in all studies. Control mortality was generally less than 10%.

Insect inhibitory activity against the cotton boll weevill (Coleoptera: *Anthomonas grandis*) was tested as follows. *Xenorhabdus* supernatant, control medium (BHI) or tris, pH 7.0, were applied in 20 µl aliquots to the surface of 200 ul of artificial diet (Bioserv™ Co., Frenchtown, N.J.; diet product F9247) and allowed to air-dry. Boll weevil eggs were then placed into the wells, the wells sealed and the plates held at 27° C., 60% relative humidity (RH) for 6 days. An activity score, based on confounding of frass production, growth and mortality was then assessed and analyzed statistically (SAS institute, 1989-1997. User's manual for JMP version 3.2). Control mortality ranged between 0-25%.

The bacterial culture supernatant was also active against Lepidopteran larvae, such as the cotton bollworm, corn earworm, beet armyworm, and black cutworm, which are members of the Noctuidae family. Other Noctuids include the armyworms of the genus *Spodoptera*, and the loopers such as the cabbage looper. Activity was also observed against the European corn borer, a member of the Pyralidae family. Other Pyralids include the southwestern corn borer, the rice yellow stem borer, the pink stem borer, leaf rollers, and the Asiatic striped stem borer. Other typical members of the order Lepidoptera are the codling moth, clothes moth, Indian meal moth, cabbage worm, bagworm, Eastern tent caterpillar, sod webworm, and tobacco and tomato hornworms.

Insect inhibitory activity against Lepidopteran larvae was tested as follows. *Xenorhabdus* culture supernatant, control medium (BHI) and Tris buffer, pH 7.0, were applied directly to the surface (about 0.38 cm2) of standard artificial Lepidopteran diet (Southland Products Incorporated, Lake Village Ark.; diet product Lepidopteran multi-species diet) in 20 µl aliquots. The diet plates were allowed to air-dry in a drying chamber (16-20° C.; 40-50% RH). The test wells were then infested with insect eggs, suspended in agar, of tobacco bud worm (*Heliothis virescens*), corn ear worm (*Helicoverpa zea*) or black cut worm (*Agrotis ipsylon*). In the case of European corn borer (Lepidoptera: *Ostrinia nubilalis*), neonates were hand infested into the wells at one neonate per well. Following infestation, diet plates were sealed, placed in a humidity controlled growth chamber and maintained in the dark at 27° C. for the appropriate period of time. Mortality and stunting measurements were scored at day 5 and statistically analyzed (SAS institute, 1989-1997. User's manual for JMP version 3.2). Generally 24 insects per treatment were used in all studies. Control mortality generally ranged from 0-12.5%.

Insect inhibitory activity was also demonstrated against *Lygus* bug, a member of the order Hemiptera. Other members of the order include the stink bugs, seed bugs, chinch bugs, and stainers.

Insect inhibitory activity against *Lygus* bug (Hemiptera: *Lygus hesperus*), was tested as follows. Feeding domes were made using a dome-making machine manufactured by Analytical Research Systems, Gainesville Fla. Briefly, the system uses a vacuum to form domes from Parafilm™ sheeting using an aluminum block template shaped in the form of a 96-well microtiter-plate. To each such formed dome was added 40 ul of a 1:10 (v/v) dilution of test solution in diet. The dome-molded Parafilm™ is then heat sealed with a sheet of Mylar. The resulting Parafilm dome sheet (96-wells) is placed onto a 96-well flat-bottomed microtiter plate containing one *Lygus* nymph each. The assay is typically scored after 4 days for mortality and stunting (0-3). Insect inhibition results from all tests were shown in Table 7 of the US Patent Application Publication No. 20110167520 A1, which is incorporated herein by reference in its entirety.

EXAMPLE 7

This example illustrates the alignment of insect inhibitory amino acid sequences identified from publicly available databases to sequences encoded by genomic sequences disclosed herein. Also, thermal amplification primers are described based on conserved regions identified in the alignments which can be used to isolate DNA sequences encoding insect inhibitory proteins from both *Xenorhabdus* and *Photorhabdus* species. Surprisingly, primers designed to isolate insect inhibitory proteins based on regions of substantial homology between proteins from diverse species fail to produce amplification products from strains which are believed to be phylogenetically more closely related and which have been shown to produce insect inhibitory proteins active against the same target pest insect species. In this example, *Xenorhabdus* and *Photorhabdus* strains other than strain Xs85816 and W14 were selected for thermal amplification and southern blot analysis based on their having demonstrated activity against southern corn rootworm.

Translation of *Xenorhabdus* genomic data indicated several sequences encoding proteins which exhibited homologies to previously identified *Photorhabdus* insect inhibitory polypeptides available in public databases such as GenBank (see, for example, Table 2 of the aforementioned US Patent Application Publication No. 20110167520 A1). Thermal amplification primers were designed to amplify DNA sequences from within insect inhibitory coding sequences. Based on *Xenorhabdus* sequences which were aligned with *Photorhabdus* sequences, the top BLAST hits were used along with regions of greatest amino acid sequence conservation for primer design. *Xenorhabdus* polypeptide XIP8 most closely aligned with polypeptide TccB from *Photorhabdus* strain W14. Based on this alignment, regions of greatest amino acid sequence homology were used to design a XIP-8 primer set consisting of the primers as disclosed in the US Patent Application Publication No. 20110167520 A1, which is incorporated herein by reference in its entirety. As indicated therein, this primer set amplified DNA xip8 sequences from *Xenorhabdus* strain Xs85816 but not from other *Xenorhabdus* strains or from at least one other *Photorhabdus* strain. Interestingly, a primer set designed from regions of identity between XIP9 and XIP10 protein coding sequences comprising the primers as disclosed in the aforementioned US Patent Application Publication No. 20110167520 A1 was able to amplify xip9 and xip10 coding sequences from *Xenorhabdus* strain Xs85816 as well as sequences from several other *Xenorhabdus* strains. However, the XIP9/10 primer set failed to amplify sequences from every *Xenorhabdus* or *Photorhabdus* strain analyzed, even though degeneracies (R=A+G, Y=C+T, W=A+T) were engineered into the primer set to compensate for possible wobble. A further primer set similar in nature to the set designed for XIP9 and XIP10 was also designed from DNA sequences encoding regions of amino acid sequence identity between XIP1 and XIP2 consisting of the primers as disclosed in the aforementioned US Patent Application Publication No. 20110167520 A1. Primer set XIP1/2 failed to amplify any sequences from *Xenorhabdus* or *Photorhabdus* strains other than *Xenorhabdus* strain Xs85816.

The product derived from thermal amplification of Xs85816 genomic DNA using the primers designed to amplify XIP8 coding sequences was labeled and used to probe total genomic DNA from Xs85816 as well as other *Xenorhabdus* and *Photorhabdus* strains. A thermal amplification product derived from *Xenorhabdus* strain Xs85816 ompR, a highly conserved gene at the DNA sequence level among gram negative Enterobacteriaceae, was used as a control. The ompR sequence was able to hybridize to sequences in all strains analyzed, however, the xip8 sequence failed to hybridize to any sequences in the strains tested other than Xs85816. In addition, ompR thermal amplification primers based on the ompR gene in Xs85816 also amplified a sequence of equivalent size from each strain tested. These results, taken together, suggest a large diversity in the proteins exhibiting insect inhibitory activity from both *Xenorhabdus* and *Photorhabdus* species.

SEQUENCE LISTING

<160> NUMBER OF SEQ ID NOS: 2

<210> SEQ ID NO 1
<211> LENGTH: 1670
<212> TYPE: DNA
<213> ORGANISM: Xenorhabdus sp.
<220> FEATURE:
<221> NAME/KEY: CDS
<222> LOCATION: (653)..(1537)
<223> OTHER INFORMATION: GroEL coding sequence

<400> SEQUENCE: 1

| | | |
|---|---|---|
| gatggtaatc atggtcagac atttgaagga gagtatgagc gcaggcagga tgatgcttcg | 60 | |
| aataagatta ctcgcgatga tcaaaaaaat cataatgagt atgataatga ccacaataag | 120 | |
| aaataacttc agctcatact gtctgagatt gtcacgggta ataaaaaagt gaaatatttt | 180 | |
| ttgctatccc cccttgaagt actgcctata agccccaact tgtagcttca tggtactggt | 240 | |
| tctgttgggt tctggtatca atcctcttac ctgatatgga ctttatttat aggagatcta | 300 | |
| tcaatgaaaa ttcgtccatt acacgaccgt gttatcgtca aacgtcaaga agttgaatct | 360 | |
| aaatctgctg gtggaatcgt tctgaccggt tcagctgcgg gcaaatctac ccgtggtgaa | 420 | |
| gttcttgctg ttggccatgg tcgcatcctg gaaagcggtg atgttaaagc tctggatgtt | 480 | |
| aaagtgggtg atatcgttat ttttaatgaa ggttacggtg ttaaagcaga agatcgat | 540 | |
| aacgaagaag tgttgatcat gtctgaaagc gatattctgg caattgttga agcgtaattg | 600 | |
| aaaatcttac gctcagatct tcttaactga acgaattta aggaaagata ca atg gca | 658 | |
|  | Met Ala | |
|  | 1 | |
| gct aaa gac gta aaa ttt ggt aat gat gct cgc agc aaa atg ttg cgt | 706 | |
| Ala Lys Asp Val Lys Phe Gly Asn Asp Ala Arg Ser Lys Met Leu Arg | | |
| 5                     10                 15 | | |
| ggt gtg aat gta ctg gct gat gca gtt aaa gtg act ctg ggt cct aaa | 754 | |
| Gly Val Asn Val Leu Ala Asp Ala Val Lys Val Thr Leu Gly Pro Lys | | |
| 20                 25                 30 | | |
| ggc cgt aat gtt gtt ttg gat aaa tct ttt ggt gca cct gta att act | 802 | |
| Gly Arg Asn Val Val Leu Asp Lys Ser Phe Gly Ala Pro Val Ile Thr | | |
| 35                 40                 45                 50 | | |
| aaa gat ggt gtt tct gta gca cgt gaa atc gaa tta gaa gat aaa ttc | 850 | |
| Lys Asp Gly Val Ser Val Ala Arg Glu Ile Glu Leu Glu Asp Lys Phe | | |
|                 55                 60                 65 | | |
| gaa aac atg ggt gca cag atg gtt aaa gaa gtt gct tct aaa gct aac | 898 | |
| Glu Asn Met Gly Ala Gln Met Val Lys Glu Val Ala Ser Lys Ala Asn | | |
|             70                 75                 80 | | |
| gat gcg gct ggt gat ggt aca act act gca acc gtt ctg gcc caa gca | 946 | |
| Asp Ala Ala Gly Asp Gly Thr Thr Thr Ala Thr Val Leu Ala Gln Ala | | |
|         85                 90                 95 | | |
| atc gtc acc gaa ggt ctg aaa gca gtt gct gct ggc atg aac cca atg | 994 | |
| Ile Val Thr Glu Gly Leu Lys Ala Val Ala Ala Gly Met Asn Pro Met | | |
|     100                 105                 110 | | |
| gat ctg aaa cgt ggt att gat aaa gca gtt gtt tcc gct gtt gaa gaa | 1042 | |
| Asp Leu Lys Arg Gly Ile Asp Lys Ala Val Val Ser Ala Val Glu Glu | | |
| 115                 120                 125                 130 | | |
| ctg aaa aaa ctg tcc gta cct tgc tct gat tcc act gca att gca cag | 1090 | |
| Leu Lys Lys Leu Ser Val Pro Cys Ser Asp Ser Thr Ala Ile Ala Gln | | |
|                 135                 140                 145 | | |
| gtt ggt aca atc tct gca aac tcc gac gaa act gtt ggt aaa ctg atc | 1138 | |
| Val Gly Thr Ile Ser Ala Asn Ser Asp Glu Thr Val Gly Lys Leu Ile | | |
|             150                 155                 160 | | |

| | | | | | | | | | | | | | | | | |
|---|---|---|---|---|---|---|---|---|---|---|---|---|---|---|---|---|
| gca | gaa | gcg | atg | gat | aaa | gtc | ggt | aaa | gaa | ggt | gta | atc | act | gtt | gaa | 1186 |
| Ala | Glu | Ala | Met | Asp | Lys | Val | Gly | Lys | Glu | Gly | Val | Ile | Thr | Val | Glu | |
| | 165 | | | | 170 | | | | 175 | | | | | | | |

| | | | | | | | | | | | | | | | | |
|---|---|---|---|---|---|---|---|---|---|---|---|---|---|---|---|---|
| gaa | ggt | act | ggt | ctg | gaa | gac | gaa | ctg | gat | gtt | gtt | gaa | ggt | atg | cag | 1234 |
| Glu | Gly | Thr | Gly | Leu | Glu | Asp | Glu | Leu | Asp | Val | Val | Glu | Gly | Met | Gln | |
| 180 | | | | | 185 | | | | | 190 | | | | | | |

| | | | | | | | | | | | | | | | | |
|---|---|---|---|---|---|---|---|---|---|---|---|---|---|---|---|---|
| ttc | gac | cgt | ggt | tac | ctg | tct | cct | tat | ttc | atc | aac | aaa | cca | gaa | tca | 1282 |
| Phe | Asp | Arg | Gly | Tyr | Leu | Ser | Pro | Tyr | Phe | Ile | Asn | Lys | Pro | Glu | Ser | |
| 195 | | | | 200 | | | | | 205 | | | | | 210 | | |

| | | | | | | | | | | | | | | | | |
|---|---|---|---|---|---|---|---|---|---|---|---|---|---|---|---|---|
| ggt | tct | gtt | gaa | ctg | gaa | aac | cca | tac | atc | ctg | ttg | gta | gac | aaa | aaa | 1330 |
| Gly | Ser | Val | Glu | Leu | Glu | Asn | Pro | Tyr | Ile | Leu | Leu | Val | Asp | Lys | Lys | |
| | | | 215 | | | | | 220 | | | | | 225 | | | |

| | | | | | | | | | | | | | | | | |
|---|---|---|---|---|---|---|---|---|---|---|---|---|---|---|---|---|
| gtt | tcc | aac | atc | cgt | gaa | ctg | ttg | cca | gtt | ctg | gaa | ggt | gta | gct | aaa | 1378 |
| Val | Ser | Asn | Ile | Arg | Glu | Leu | Leu | Pro | Val | Leu | Glu | Gly | Val | Ala | Lys | |
| | | 230 | | | | | 235 | | | | | 240 | | | | |

| | | | | | | | | | | | | | | | | |
|---|---|---|---|---|---|---|---|---|---|---|---|---|---|---|---|---|
| gca | agc | aaa | cct | ctg | ctc | atc | atc | gct | gaa | gat | gtt | gaa | ggc | gaa | gcg | 1426 |
| Ala | Ser | Lys | Pro | Leu | Leu | Ile | Ile | Ala | Glu | Asp | Val | Glu | Gly | Glu | Ala | |
| | 245 | | | | | 250 | | | | | 255 | | | | | |

| | | | | | | | | | | | | | | | | |
|---|---|---|---|---|---|---|---|---|---|---|---|---|---|---|---|---|
| ctg | gct | act | ctg | gtt | gtg | aac | aac | atg | cgt | ggt | atc | gtg | aaa | gtt | gct | 1474 |
| Leu | Ala | Thr | Leu | Val | Val | Asn | Asn | Met | Arg | Gly | Ile | Val | Lys | Val | Ala | |
| 260 | | | | | 265 | | | | | 270 | | | | | | |

| | | | | | | | | | | | | | | | | |
|---|---|---|---|---|---|---|---|---|---|---|---|---|---|---|---|---|
| gcg | gtt | aaa | cac | cag | gtt | tcg | gtg | atc | gcc | gta | aag | caa | tgc | tgc | agg | 1522 |
| Ala | Val | Lys | His | Gln | Val | Ser | Val | Ile | Ala | Val | Lys | Gln | Cys | Cys | Arg | |
| 275 | | | | 280 | | | | | 285 | | | | | 290 | | |

| | | | | |
|---|---|---|---|---|
| ata | ttg | cta | tcc | tga ctaacggtac tgttatttct gaagagattg gtctggagct | 1577 |
| Ile | Leu | Leu | Ser | | | ggaaaaagca actctggaag atctgggtca ggcaaaacgt gttgttatca acaaagacac      1637 cactactatc attgatggcg taagcgaagc aag      1670

<210> SEQ ID NO 2
<211> LENGTH: 294
<212> TYPE: PRT
<213> ORGANISM: Xenorhabdus sp.

<400> SEQUENCE: 2

Met Ala Ala Lys Asp Val Lys Phe Gly Asn Asp Ala Arg Ser Lys Met
1               5                   10                  15

Leu Arg Gly Val Asn Val Leu Ala Asp Ala Val Lys Val Thr Leu Gly
                20                  25                  30

Pro Lys Gly Arg Asn Val Val Leu Asp Lys Ser Phe Gly Ala Pro Val
            35                  40                  45

Ile Thr Lys Asp Gly Val Ser Val Ala Arg Glu Ile Glu Leu Glu Asp
        50                  55                  60

Lys Phe Glu Asn Met Gly Ala Gln Met Val Lys Glu Val Ala Ser Lys
65                  70                  75                  80

Ala Asn Asp Ala Ala Gly Asp Gly Thr Thr Thr Ala Thr Val Leu Ala
                85                  90                  95

Gln Ala Ile Val Thr Glu Gly Leu Lys Ala Val Ala Ala Gly Met Asn
            100                 105                 110

Pro Met Asp Leu Lys Arg Gly Ile Asp Lys Ala Val Val Ser Ala Val
        115                 120                 125

Glu Glu Leu Lys Lys Leu Ser Val Pro Cys Ser Asp Ser Thr Ala Ile
    130                 135                 140

Ala Gln Val Gly Thr Ile Ser Ala Asn Ser Asp Glu Thr Val Gly Lys
145                 150                 155                 160

Leu Ile Ala Glu Ala Met Asp Lys Val Gly Lys Glu Gly Val Ile Thr
                165                 170                 175

-continued

| | | | | | | | | | | | | |
|---|---|---|---|---|---|---|---|---|---|---|---|---|
|Val|Glu|Glu|Gly<br>180|Thr|Gly|Leu|Glu|Asp<br>185|Glu|Leu|Asp|Val<br>190|Val|Glu|Gly|
|Met|Gln|Phe<br>195|Asp|Arg|Gly|Tyr|Leu<br>200|Ser|Pro|Tyr|Phe|Ile<br>205|Asn|Lys|Pro|
|Glu|Ser|Gly<br>210|Ser|Val|Glu|Leu<br>215|Glu|Asn|Pro|Tyr|Ile<br>220|Leu|Leu|Val|Asp|
|Lys<br>225|Lys|Val|Ser|Asn|Ile<br>230|Arg|Glu|Leu|Leu|Pro<br>235|Val|Leu|Glu|Gly|Val<br>240|
|Ala|Lys|Ala|Ser|Lys<br>245|Pro|Leu|Leu|Ile|Ile<br>250|Ala|Glu|Asp|Val|Glu<br>255|Gly|
|Glu|Ala|Leu|Ala<br>260|Thr|Leu|Val|Val|Asn<br>265|Asn|Met|Arg|Gly|Ile<br>270|Val|Lys|
|Val|Ala|Ala<br>275|Val|Lys|His|Gln|Val<br>280|Ser|Val|Ile|Ala|Val<br>285|Lys|Gln|Cys|
|Cys|Arg<br>290|Ile|Leu|Leu|Ser| | | | | | | | | | |

What is claimed is:

1. An isolated nucleic acid molecule comprising:
   a) a nucleic acid encoding a GroEL polypeptide having at least 95% identity with the amino acid sequence of SEQ ID NO: 2, wherein said GroEL polypeptide has chaperonin activity; or
   b) the complement of the nucleic acid of a).

2. The nucleic acid molecule of claim 1, wherein said nucleic acid has at least 95% sequence identity with SEQ ID NO: 1.

3. The nucleic acid molecule of claim 2, wherein said nucleic acid has at least 98% sequence identity with SEQ ID NO: 1.

4. The nucleic acid molecule of claim 3, wherein said nucleic acid is 100% identical to SEQ ID NO: 1.

5. A transformed host cell comprising the nucleic acid molecule of claim 1.

6. The transformed host cell of claim 5, wherein said host cell is selected from the group consisting of a plant cell, a mammalian cell, a bacterial cell, an algal cell, an insect cell an a fungal cell.

7. A transgenic plant comprising the nucleic acid molecule of claim 1.

8. The transgenic plant of claim 7, further comprising a 5' non-coding sequence which functions in a plant to cause the production of a mRNA molecule, said 5' non-coding sequence operably linked to said nucleic acid molecule, which is further operably linked to a 3' non-translated sequence that functions in said plant to cause termination of transcription.

9. The transgenic plant of claim 7, wherein said plant is a monocot or a dicot plant.

10. A seed produced from the plant of claim 7, wherein said seed comprises said nucleic acid molecule.

11. A progeny plant from the seed of claim 10, wherein said progeny comprises said nucleic acid molecule.

* * * * *